(12) United States Patent
Barnett et al.

(10) Patent No.: US 9,993,401 B2
(45) Date of Patent: Jun. 12, 2018

(54) BENEFIT DELIVERY PARTICLE, PROCESS FOR PREPARING SAID PARTICLE, COMPOSITIONS COMPRISING SAID PARTICLES AND A METHOD FOR TREATING SUBSTRATES

(71) Applicant: Conopco, Inc., Englewood Cliffs, NJ (US)

(72) Inventors: Stuart Anthony Barnett, Bebington (GB); Craig Warren Jones, Bebington (GB); Adam John Limer, Shanghai (CN); James Merrington, Bebington (GB); Jeremy Nicholas Winter, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 21 days.

(21) Appl. No.: 14/482,545

(22) Filed: Sep. 10, 2014

(65) Prior Publication Data

US 2014/0378369 A1    Dec. 25, 2014

Related U.S. Application Data

(63) Continuation of application No. 13/809,447, filed as application No. PCT/EP2011/061782 on Jul. 11, 2011, now abandoned.

(30) Foreign Application Priority Data

Jul. 15, 2010 (GB) .................................. 1011905.5

(51) Int. Cl.

| | |
|---|---|
| *A61K 8/11* | (2006.01) |
| *B01J 13/18* | (2006.01) |
| *A61Q 19/10* | (2006.01) |
| *A61Q 13/00* | (2006.01) |
| *A61Q 5/02* | (2006.01) |
| *A61K 8/81* | (2006.01) |
| *A61K 8/87* | (2006.01) |
| *B01J 13/16* | (2006.01) |
| *C11D 3/50* | (2006.01) |
| *C11D 17/00* | (2006.01) |
| *D06M 23/12* | (2006.01) |
| *A61Q 15/00* | (2006.01) |
| *D06M 23/08* | (2006.01) |
| *A23P 10/30* | (2016.01) |
| *A23L 27/00* | (2016.01) |

(52) U.S. Cl.
CPC ............... *A61K 8/11* (2013.01); *A23L 27/72* (2016.08); *A23P 10/30* (2016.08); *A61K 8/8152* (2013.01); *A61K 8/87* (2013.01); *A61Q 5/02* (2013.01); *A61Q 13/00* (2013.01); *A61Q 15/00* (2013.01); *A61Q 19/10* (2013.01); *B01J 13/16* (2013.01); *B01J 13/18* (2013.01); *C11D 3/505* (2013.01); *C11D 17/0039* (2013.01); *D06M 23/08* (2013.01); *D06M 23/12* (2013.01); *A61K 2800/412* (2013.01); *A61K 2800/413* (2013.01); *A61K 2800/56* (2013.01); *A61K 2800/654* (2013.01)

(58) Field of Classification Search
CPC ............... A23L 1/0029; A23L 1/22016; A61K 2800/412; A61K 2800/413; A61K 2800/56; A61K 2800/654; A61K 8/11; A61K 8/8152; A61K 8/87; A61Q 13/00; B01J 13/16; B01J 13/18
See application file for complete search history.

(56) References Cited

U.S. PATENT DOCUMENTS

| | | | |
|---|---|---|---|
| 3,516,941 | A | 7/1966 | Matson |
| 4,622,267 | A | 11/1986 | Riecke |
| 7,119,057 | B2 | 10/2006 | Popplewell et al. |
| 7,807,076 | B2 | 10/2010 | Hunt et al. |

(Continued)

FOREIGN PATENT DOCUMENTS

| | | |
|---|---|---|
| EP | 1438216 B1 | 7/2006 |
| EP | 2204155 | 7/2010 |

(Continued)

OTHER PUBLICATIONS

Communication of Notice of Opposition (Henkel) in EP2593072 (EP11738424.8), dated Mar. 12, 2015.

(Continued)

*Primary Examiner* — Anna Falkowitz
(74) *Attorney, Agent, or Firm* — Greenberg Traurig, LLP

(57) ABSTRACT

The invention provides a benefit agent delivery particle having an average diameter of less than 50 micron comprising; at least one shell formed by a step-growth polymerization reaction, preferably involving an isocyanate monomer, more preferably a urethane and/or a urea. interior said shell, at least one region formed by chain-growth polymerization reaction (preferably a free-radical polymerization) which does not involve an isocyanate, c) optionally, a benefit agent interior to said shell, and/or a deposition aid exterior to said shell. The invention further provides a process for the preparation of such particles wherein the shell is formed prior to the chain-growth polymerization of the at least one region interior of the shell, preferably be forming the shell at a temperature at which the chain-growth reaction is inhibited. The invention further provides fully formulated products, preferably liquids and gels, which contain said benefit agent delivery particles and a method of treating substrates using said products.

19 Claims, No Drawings

(56) References Cited

U.S. PATENT DOCUMENTS

| | | |
|---|---|---|
| 2002/0058732 A1 | 5/2002 | Mistry et al. |
| 2002/0169233 A1 | 11/2002 | Schwantes |
| 2005/0153839 A1 | 7/2005 | Tamura |
| 2009/0304756 A1 | 12/2009 | Dahne et al. |
| 2009/0312222 A1 | 12/2009 | Ferguson et al. |
| 2010/0168251 A1* | 7/2010 | Warr .................. A61K 8/11 |
| | | 514/772 |

FOREIGN PATENT DOCUMENTS

| | | | | |
|---|---|---|---|---|
| GB | 2432850 | 6/2007 | | |
| GB | 2432851 | 6/2007 | | |
| JP | 2000503051 A | 3/2000 | | |
| JP | 2004513192 A | 4/2004 | | |
| JP | 2006510580 | 3/2006 | | |
| JP | 2009507592 | 2/2009 | | |
| JP | 2009107941 | 5/2009 | | |
| JP | 2010018604 | 1/2010 | | |
| WO | 9724177 A1 | 7/1997 | | |
| WO | 9828398 A1 | 7/1998 | | |
| WO | WO0126635 | 4/2001 | | |
| WO | 0236258 A2 | 5/2002 | | |
| WO | WO2004016232 | 2/2004 | | |
| WO | 2008145547 A1 | 12/2008 | | |
| WO | WO 2008/145547 | * 12/2008 | ............... | C11D 3/22 |
| WO | WO2009153695 | 12/2009 | | |
| WO | WO 2010/051293 | * 5/2010 | ............ | C08G 18/08 |
| WO | WO2010051293 A1 | 5/2010 | | |

OTHER PUBLICATIONS

Paul J. Flory, Principles of Polymer Chemistry, Definitions and Classifications, Cornell University Press (1953) p. 39.

\* cited by examiner

BENEFIT DELIVERY PARTICLE, PROCESS FOR PREPARING SAID PARTICLE, COMPOSITIONS COMPRISING SAID PARTICLES AND A METHOD FOR TREATING SUBSTRATES

TECHNICAL FIELD

The present invention is concerned with the delivery of particles, optionally comprising benefit agents and/or deposition aids, to substrates, with processes for the manufacture of said particles and the manufacture and use of formulations comprising the same. It will be specifically described herein with reference to laundry treatment compositions but has other and broader applications.

BACKGROUND

Many home and personal care formulations seek to deliver so-called benefit agents to substrates such as cloth, hair and skin. Encapsulation of the benefit agent in particles has been proposed as a means of enhancing delivery, which is advantageous because of the expense of some benefit agents. Delivery of particles per se can also be useful where the particles, even in the absence of specific benefit agents, confer a benefit.

These particles may comprise polymers and many different types of polymerisation are known. In the present specification a distinction will be drawn between step-growth and chain-growth polymerisation. This is the well-established reaction mechanism distinction drawn by Paul Flory in 1953 (see Paul J. Flory, "Principles of Polymer Chemistry", Cornell University Press, 1953, p. 39. ISBN 0801401348).

For the purposes of the present specification a chain-growth polymer is a polymer which is formed by a reaction in which monomers bond together via rearrangement (for example, of unsaturated and typically vinyllic bonds, or by a ring-opening reaction) without the loss of any atom or molecule. Chain-growth polymers grow in a single direction from one end of the chain only and an initiator is typically used. In chain-growth polymerisation it is commonplace that once a growth at a chain end is terminated the end becomes unreactive.

An example of one type of chain-growth polymerisation is the free-radical polymerisation reaction, for example the well-known polymerization of styrene (vinyl benzene) in the presence of benzoyl peroxide (as radical initiator) to produce polystyrene. Similarly, aluminum chloride may be used to initiate the polymerisation of isobutylene to form synthetic rubber. Other examples include the polymerization reactions of acrylates or methacryates.

A step-growth polymer is a polymer whose chain is formed during by the reaction of poly-functional monomers to form increasingly larger oligomers. Growth occurs throughout the matrix and the monomer level falls rapidly in the early stages of the reaction. No initiator is needed for a step growth polymerisation and the ends of the growing chain generally remain active at all times. Typically (but not always) a small molecule, which is often water, is eliminated in the polymerization process.

An example of step-growth polymerization is the formation of polyester by the reaction of dicarboxylic acids and glycols with elimination of water. Another example is the polymerisation of phenol and formaldehyde to produce "Bakelite". Other well known step-growth polymerisation reactions are the formation of polyesters, polyurethanes, polyureas, polyamides and polyethers.

It should be noted that chain-growth polymerisation and so-called "addition polymerisation" are different concepts. Addition polymerisation is where the reaction product is a polymer only. This may be contrasted with "condensation polymerisation" where a small molecule (the "condensate") is also produced. Polyurethane, for example, is produced by addition polymerisation of (di)isocyanate compounds (R—N=C=O) with (di)hydroxy compounds (HO—R) to form the urethane/carbamate linkage (R—NH—CO—O—R), but the reaction mechanism is step-growth rather than chain-growth as there is molecular rearrangement without elimination of a small molecule.

Both chain-growth and step-growth have been used to prepare particles by polymerisation in which some of the components are present in the dispersed phase of an emulsion. In the case of chain-growth, all of the components may be present in droplets of the dispersed phase which, once initiated, react internally to form a particle. In the case of step-growth, components may be present both in the dispersed and the continuous phase to react at the dispersed phase surface to form a "shell" at the interface.

In US 2009/312222 particles are prepared using so-called "mini-emulsion" polymerisation, to give a particle with a size as from about 30 to 500 nm. The polymer comprises units derived from monomers that are capable of undergoing chain-growth free-radical polymerisation. GB 2432851 discloses particles derived from monomers that are capable of undergoing free-radical polymerisation. GB 2432850 discloses core/shell particles in which both the core and the shell comprises monomer units which are derived from monomers that are capable of undergoing free-radical polymerisation.

Emulsion polymerisation can also be performed using step-growth reactions. U.S. Pat. No. 4,622,267 discloses an interfacial polymerization technique for preparation of microcapsules. US 2002/169233 discloses an interfacial polymerization process wherein a microcapsule wall of a polyamide, an epoxy resin, a polyurethane, a polyurea or the like is formed at an interface between two phases. The core material is initially dissolved in a solvent and an aliphatic diisocyanate soluble in the solvent mixture is added. Subsequently, a non-solvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurea shells.

Microcapsules have been proposed in which the wall material comprises both a step-growth polymer and a chain-growth polymer.

US 2005/0153839 disclose microcapsules for use in the production of multicolour thermo-sensitive recording materials having polyurethane or polyurea walls. The polymer wall includes (via a covalent bond) a polymer obtained by radically polymerising at least a vinyl monomer further comprising a polyether. Preferably the raw materials for the walls are di-isocyanates. It should be noted that the vinyl polymer is included in the wall rather than being enclosed by it.

EP 2204155 discloses leak-proof, friable core-shell fragrance microcapsules which have melamine-formaldehyde (step-growth polymer) shells and in which the core may optionally comprise, among other possibilities, high density organic oil-soluble ingredients which may be prepared by any standard means such as radical polymerisation of unsaturated monomers such as vinyl or acrylic monomers (which are chain-growth polymers). Alternatively the polymers may be prepared by condensation reactions such as those leading to polyethers or polyesters (which are step-growth polymers). The fragrance comprises at least one cyclic fragrance material. The reason for including these pre-formed high density materials is to match the density of the micro-capsules with that of the composition in which they are used, to prevent separation.

An effective encapsulate for a benefit agent, for example a benefit agent such as perfume, should have the following properties:

- It should have a target loading of 20% w/w benefit agent or better and be easy to load;
- It should minimise leakage of the benefit agent into a product during manufacture and on storage;
- It should not require modification of the bulk formulation, for example by requiring the presence of structuring and/or suspending systems;
- Ideally, the encapsulate should deposit well onto substrates;
- The encapsulate should control the release of benefit agent.

BRIEF DESCRIPTION OF THE INVENTION

We have now determined that improved particles comprise a shell which comprises a step-growth polymer (for example an isocyanate based polymer) and at least one region interior to the shell which comprises a chain-growth polymer (for example a poly(meth)acrylate). The shell may be formed by interfacial polymerisation, and the interior region by radical polymerisation. Advantageously, the polymer which comprises the shell is formed prior to the "internal" polymer.

Accordingly, the present invention provides a particle having an average diameter of less than 50 micron comprising:
a) at least one shell formed by a step-growth polymerisation reaction,
b) interior to said shell, at least one region formed by chain-growth polymerisation reaction which does not involve an isocyanate, and,
c) optionally, a benefit agent interior to the shell, and/or a surface modification exterior to said shell.

Such particles have an inner region, typically forming a "core" which provides a sink for the benefit agent and a "shell" which protects the benefit agent and regulates the flow of benefit agent into and out of the core. Thus, the particle can be a carrier which controls thermodynamic (rather than kinetic) partition of the benefit agent between the interior region and elsewhere. This is particularly advantageous where late-stage addition of perfume is required as the particles and the perfume may be dosed into the product separately.

Typically, the step-growth polymerisation reaction used to form the shell is not a condensation polymerisation, and, more preferably, involves an isocyanate monomer, more preferably a urethane and/or a urea. Isocyanate monomers are reactive, enable high monomer conversion, and form a robust, glassy shell which can survive drying and other processing. As noted above, isocyanate monomers react by a step-growth mechanism but are categorised as an addition polymer by virtue of no small molecule being eliminated during polymerisation.

Preferably, the chain-growth polymerisation reaction used to form the inner region is a radical polymerisation reaction, more preferably of at least one ethylenically unsaturated monomer, conveniently a vinyllic monomer, most preferably selected from acrylate or methacryate. Such materials enable the compatibility of the inner region (typically a "core") and the benefit agent to be optimised for desirable delivery parameters. In particular the solubility parameters of the benefit agent and the chain-growth polymer comprising the inner region may be matched to achieve improved absorption and/or delivery.

Advantageously the particle comprises, a surface modification, preferably a deposition aid. In particularly preferred embodiments the deposition aid is substantive to proteinaceous, cellulosic, polyester or polyamide surfaces. By use of such a deposition aid, the efficiency of delivery to a specific substrate may be enhanced.

Typically, the particle has an average diameter of less than 10 micron, and preferably an average diameter of less than 1 micron, more preferably less than 500 nm. One benefit of small particles is that they are less visible in clear products. Another useful benefit is that sizes below 500 nm favour deposition on fibrous substrates and can allow formulation without the need for suspending and/or structuring systems.

Advantageously the particle comprises a hydrophobic benefit agent, preferably an organoleptic benefit agent, more preferably a flavour or fragrance.

As noted above the benefit agent may be introduced into the particle during particle formation, or may be introduced into "empty" particles after particle formation.

Particles according to the present invention may be formed from an emulsion by carrying out an interfacial step-growth polymerisation first to form a shell under conditions where the chain-growth polymerisation is inhibited. Subsequently, the conditions are changed such that the material within the shell undergoes the chain-growth polymerisation. A suitable change in conditions is to increase the temperature from one at which the chain growth reaction is inhibited to one at which it proceeds. Other possible changes of conditions would be, for example, to use a chain-growth reaction which is light dependent rather than temperature dependent.

A preferred embodiment of the present invention provides a particle obtainable by a method comprising:
a) forming an emulsion, preferably having a mean dispersed particle size diameter of less than 1000 nm, more preferably less than 500 nm and having a dispersed non-aqueous phase comprising:
  i) a first co-monomer, preferably an isocyanate monomer, capable of step-growth polymeriation with a suitable second co-monomer,
  ii) an optional benefit agent, preferably an organoleptic benefit agent,
  iii) at least one monomer, preferably acrylate or methacryate, capable of chain-growth polymerisation, and
  iv) a radical initiator, preferably peroxide or azo-, which is not significantly active at the temperature at which the first co-monomer undergoes step-growth polymerisation
  and, a continuous aqueous phase comprising:
  i) water,
  ii) an emulsifying agent,
  iii) a second co-monomer for the first co-monomer, preferably a diol or diamine,
b) maintaining the emulsion at a temperature at which the step-growth polymerisation occurs but not the chain growth polymerisation, and, subsequently,
c) maintaining the emulsion at a temperature at which the chain-growth polymerisation proceeds.

Preferably the first and second co-monomers react by a step-growth mechanism to form a poly-urethane (which may be illustrated by the approximate formula (—R$_1$—NH—CO—O—R$_2$—O—CO—NH—)$_n$) or a polyurea (which may be illustrated by the approximate general formula (—NH—CO—NH—R—)$_n$).

The monomer capable of chain-growth polymerisation is preferably ethylenically unsaturated, more preferably vinyllic. In the alternative, a ring-opening mechanism may be used.

Advantageously, the above described method provides a potentially "one-pot" reaction which has the advantages of simplicity and reduced losses: i.e. the shell is formed by step-growth polymerisation at the interface of the emulsion droplets and the core is subsequently formed within the shell by an in-situ chain-growth polymerisation.

Conveniently the particle further comprises a cross-linking agent, derived from a more than di-functional species having isocyanate, alcohol, amine functionality, and/or a more than mono-functional vinyllic monomer. Tri- and tetra-functional materials are preferred. The benefit of cross-linking agents is to increase robustness of either the shell or the inner region, and or decrease permeability. Cross-linking agents in the shell, particularly the poly-functional isocyanates, can dramatically reduce the possibility of leakage. Cross linking agents in the inner region can modify interaction of the "core" with the benefit agent, e.g. by modification of the solubility parameters.

A further aspect of the invention provides a process for the manufacture of a product comprising the particles according to the invention wherein the particles and the benefit agent are added separately to the formulation.

A further aspect of the present invention provides a method of treatment of a substrate, preferably wherein the substrate is selected from skin, hair and/or textile material, which includes the step of treating the substrate with a composition comprising particles according to the present invention.

Because of the robustness of the particles of the present invention, they can be formulated in products which have relatively harsh environments, such as high solvent content, bleaches and/or extremes of pH. The particles are also resistant to mechanical disruption such as may occur during product processing, transport, storage or use, particularly on application to skin, hair or a textile.

A yet further aspect of the present invention provides a home or personal care composition comprising at least one particle according to the present invention, more preferably a laundry detergent, laundry conditioner, deodorant, antiperspirant, shampoo, hair conditioner or skin care or skin cleansing product.

As the particles of the present invention can be small, especially below 500 nm, they do not require suspending agents and thereby simplify product formulation and enable the production of clear/transparent products. Miniemulsion particles can be a small as 50 nm.

DETAILED DESCRIPTION OF THE INVENTION

In order that the present invention may be further and better understood it will be further described below with reference to specific embodiments of the invention and further preferred and/or optional features. All amounts quoted are wt. % of total composition unless otherwise stated.

Except in the operating and comparative examples, or where otherwise explicitly indicated, all numbers in this description indicating amounts or ratios of material or conditions of reaction, physical properties of materials and/or use are to be understood as modified by the word "about".

Step Growth Polymers:

As noted above the step-growth polymer (which comprises the "shell") is formed from monomers by the formation of increasingly larger oligomers. Suitable classes of such monomers are found in the group consisting of the melamine/urea/formaldehyde class, the isocyanate/diol class (especially the polyurethanes) and polyesters. Preferred are the melamine/urea formaldehyde class, the isocyanate/diamine class and other classes of monomers which form polyurethanes.

Suitable monomer compounds include: urea, thiourea, dicyan-diamide, melem (1,3,4,6,7,9,9b-Heptaazaphenalene), melam (N2-(4,6-diamino-1,3,5-triazin-2-yl)-1,3,5-Triazine-2,4,6-Triamine), melon (where the heptazine is polymerized with the tri-s-triazine units linked through an amine link), ammeline (4,6-Diamino-2-hydroxy-1,3,5-triazine), ammelide (6-Amino-2,4-Dihydroxy-1,3,5-Triazine), substituted melamines, guanamines, or mixtures thereof.

Substituted melamines include the alkyl melamines and aryl melamines which can be mono, di-, or tri-substituted. In the alkyl-substituted melamines, each alkyl group can contain from 1 to 6 carbons, preferably from 1 to 4 carbons. Representative examples of some alkyl-substituted melamines are monomethylmelamine, dimethyl melamine, trimethyl melamine, monoethyl melamine, and 1-methyl-3-propyl-5-butyl melamine.

In the aryl-substituted melamines, each aryl group can contain 1-2 phenyl moieties and, preferably, 1 phenyl moiety. Typical examples of an aryl-substituted melamine are monophenyl melamine or diphenyl melamine.

Especially suitable step-growth polymers are those whose isocyanate monomers are aromatic polyisocyanates, aliphatic polyisocyanates, and mixtures thereof.

Suitable, aromatic polyiscocyanates comprise, but are not limited to, 2,4- and 2,6-toluene diisocyanate, naphthalene diisocyanate, diphenyl methane diisocyanate and triphenyl methane-p,p' p"-trityl triisocyanate, polymethylene polyphenylene isocyanate, 2,4,4'-diphenylether triisocyanate, 3,3'-dimethyl-4,4'-diphenyl diisocyanate, 3,3'-dimethoxy-4,4'diphenyl diisocyanate, and 4,4'4"-triphenylmethane triisocyanate.

Suitable aliphatic polyisocyanates comprise, but are not limited to Dicyclohexylmethane 4,4'-diisocyanate, hexamethylenel,6-diisocyanate, isophorone diisocyanate, trimethyl-hexamethylene diisocyanate, trimer of hexamethylenel,6-diisocyanate, trimer of isophorone diisocyanate, 1,4-cyclohexane diisocyanate, urea of hexamethylene diisocyanate, trimethylene diisocyanate, propylene-1,2-diisocyanate and butylenel,2-diisocyanate and mixtures thereof.

The preferred isocyanate materials are: 2,4- and 2,6-toluene diisocyanate and isophorone diisocyanate.

The co-monomer used in the step-growth polymerisation is typically a diol or a diamine.

Suitable diols can comprise, but are not limited to, low molecular weight polymers such as ethylene glycol, diethylene glycol, propylene glycol, 1,4-butanediol, 2,3-butane diol, neopentyl glycol, 1,6-hexanediol, dipropylene glycol, cyclohexyll,4-dimethanol, 1,8-octanediol; high molecular weight polyols such as polyethylene glycol, polypropylene glycols, polytetramethylene glycols (PTMG) having average molecular weight in the range of 200 to 2000, polyester diols, diols containing carboxyl groups such as dimethylol propionic acid (DMPA) and dimethylol butanoic acid (DMBA) and mixtures thereof.

The preferred diol materials are ethylene glycol, diethylene glycol, propylene glycol, 1,4-butanediol, 2,3-butanediol, neopentyl glycol, 1,6-hexanedol, and dipropylene glycol. The more hydrophobic dials (particularly 1,4-butanediol, 2,3-butane diol, neopentyl glycol and 1,6-hexanediol) are preferred as it is generally easier to get a stable emulsion with these materials and thereby a more efficient polymerisation.

Suitable diamines can comprise amines such as ethylene diamine (EDA), phenylene diamine, toluene diamine, hexamethylene diamine, diethylenetriamine, tetraethylene pentaamine, pentamethylene hexamine, 1,6-hexane diamine, Methylene tetramine, 2,4-diamino-6-methyl-1,3,5 triazine 1,2-diaminocyclohexane, 4,4'-diamino-diphenylmethane, 1,5-diaminonaphthalene, 2,4,4'-triaminodiphenylether, bis(hexa-methylenetriamine), tetraminoanthraquinone, isophorone diamine, diamino propane and diaminobutane, and mixtures thereof.

The preferred diamine materials are ethylene diamine and 1,6-hexane diamine.

Mole ratios of the co-monomers are preferably selected such that the water soluble monomer is present in up to 10 mol % excess over the oil soluble co-monomer, preferably 1 to 8 mol % excess, more preferable 2 to 5 mol % excess. It is believed that this ensures complete reaction of isocyanate monomer.

Cross-Linking Agents for Step Growth Polymerisation:

As noted above cross-linking agents advantageously improve the properties of the shell. Many cross-linking agents suitable for use in step-growth polymerisation are known. Cross-linking agents significantly reduce the leakage of benefit agents from the particles. Cross-linking agents are preferably polyamines and polyols.

Preferred amine-functional cross-linking agents contains more than two amine functionalities such as tetraethylene pentamine, triethylene tetraamine, 2,4,4'-triaminodiphenylether, bis(hexamethylene triamine), 1,4,5,8-tetramino anthraquinone and diethylene triamine (DETA), and mixtures thereof.

Preferred alcohol-functional cross-linking agents contain more than two alcohol functionalities such as glycerol, pentaerythritol, and 1,1,1 trihydroxmethylpropane.

A particularly preferred cross-linking agent is polyphenylisocyanate.

The preferred levels of cross-linking agent are 1-50 mol %, more preferably 2-35 mol % of the step-growth monomers.

Chain Growth Polymers:

As noted above at least one region interior to the shell is formed by chain-growth polymerisation. Typically this will comprise a single solid region making-up the "core" of the particle.

Free-radical polymerisation (FRP) is a suitable method of chain-growth polymerisation. In FRP a mono-functional monomer is polymerised in the presence of free-radical initiator and, optionally, a chain transfer agent. Chain transfer agents can act to reduce the average molecular weight of the final polymer.

The use of a separate chain transfer agent and an initiator is preferred. However, some molecules can perform both these functions.

The free-radical initiator can be any molecule known to initiate free-radical polymerisation such as azo-containing molecules, persulfates, redox initiators, peroxides, benzyl ketones. These initiators may be activated via thermal, photolytic or chemical means. In the method of the present invention, thermal activation is preferred.

Examples of suitable initiators include but are not limited to 2,2'-azobisisobutyronitrile (AIBN), azobis(4-cyanovaleric acid), benzoyl peroxide, cumylperoxide, 1-hydroxy-cyclohexyl phenyl ketone, hydrogen peroxide/ascorbic acid.

So-called 'iniferters' such as benzyl-N,N-diethyldithiocarbamate can also be used.

In some cases, more than one initiator may be used.

The preferred initiators are: 2,2'-Azobis(2-methylbutyronitrile), 2,2'-Azobis(2,4-dimethyl valeronitrile), 1,1'-Azobis(cyclohexane-1-carbonitrile) and t-butyl hydro-peroxide/ascorbic acid as these minimise the production of unwanted bi-products.

Preferably, the residue of the initiator in a free-radical polymerisation comprises 0 to 5% w/w, preferably 0.01 to 5% w/w and especially 0.01 to 3% w/w, of the resulting copolymer based on the total weight of the monomers.

The chain transfer agent is preferably a thiol-containing molecule and can be either mono-functional or multi-functional. The agent may be hydrophilic, hydrophobic, amphiphilic, anionic, cationic, neutral or zwitterionic. The molecule can also be an oligomer containing a thiol moiety.

Suitable thiols include but are not limited to $C_2$-$C_{18}$ alkyl thiols such as dodecane thiol, thioglycolic acid, thioglycerol, cysteine and cysteamine. Thiol-containing oligomers may also be used such as oligo(cysteine) or an oligomer which has been post-functionalised to give a thiol group(s), such as oligoethylene glycolyl (di)thio glycollate. Xanthates, dithioesters, and dithiocarbonates may also be used, such as cumyl phenyldithioacetate.

Alternative chain transfer agents may be any species known to limit the molecular weight in a free-radical addition polymerisation. Thus the chain-transfer agent may also be a hindered alcohol, halocarbon, alkyl halide or a transition metal salt or complex, or similar free-radical stabiliser. Catalytic chain transfer agents such as those based on transition metal complexes such as cobalt bis(borondi-fluorodimethyl-glyoximate) may also be used.

More than one chain transfer agent may be used in combination.

The residue of the chain transfer agent may comprise 0 to 20 mole %, preferably 0 to 10 mole % and especially 0 to 3 mole %, of the copolymer (based on the number of moles of mono-functional monomer). In some cases, for example in the case of some so-called living polymerisation methods, a chain transfer agent is not required.

Monomers for the chain-growth polymerisation may comprise any carbon-carbon unsaturated (or cyclic) compound which can form an addition polymer, e.g. vinyl and allyl compounds. The mono-functional monomer may be hydrophilic, hydrophobic, amphiphilic, anionic, cationic, neutral or zwitterionic in nature. Thus, the mono-functional monomer may be selected from but not limited to monomers such as vinyl acids, vinyl acid esters, vinyl aryl compounds, vinyl acid anhydrides, vinyl amides, vinyl ethers, vinyl amines, vinyl aryl amines, vinyl nitriles, vinyl ketones, and derivatives of the aforementioned compounds as well as corresponding allyl variants thereof.

Other suitable mono-functional monomers for the chain-growth polymer include hydroxyl-containing monomers and monomers which can be post-reacted to form hydroxyl groups, acid-containing or acid functional monomers, zwitterionic monomers and quaternised amino monomers.

Oligomeric or oligo-functionalised monomers may also be used, especially oligomeric (meth)acrylic acid esters such as mono(alk/aryl) (meth)acrylic acid esters of oligo[alkyleneglycol] or oligo[dimethylsiloxane] or any other monovinyl or allyl adduct of a low molecular weight oligomer. Mixtures of more than one monomer may also be used.

Preferred vinyl acids and derivatives thereof include (meth)acrylic acid and acid halides thereof such as (meth) acryloyl chloride.

Preferred vinyl acid esters and derivatives thereof include C1-20 alkyl(meth)acrylates (linear & branched) such as methyl (meth)acrylate, stearyl (meth)acrylate and 2-ethyl hexyl (meth)acrylate, aryl(meth)acrylates such as benzyl (meth)acrylate, tri(alkyloxy)silylalkyl (meth)acrylates such as trimethoxysilylpropyl(meth)acrylate and activated esters of (meth)acrylic acid such as N-hydroxysuccinamido (meth) acrylate. Vinyl aryl compounds and derivatives thereof include styrene, acetoxystyrene, styrene sulfonic acid, vinyl pyridine, vinylbenzyl chloride and vinyl benzoic acid. Vinyl acid anhydrides and derivatives thereof include maleic anhydride. Vinyl amides and derivatives thereof include (meth) acrylamide, N-vinyl pyrrolidone, N-vinyl formamide, (meth)acrylamidopropyl trimethyl ammonium chloride, [3-((meth)acrylamido)propyl]dimethyl ammonium chloride, 3-[N-(3-(meth) acrylamidopropyl)-N,N-dimethyl]aminopropane sulfonate, methyl (meth) acrylamidoglycolate methyl ether and N-isopropyl(meth)acrylamide.

Vinyl ethers and derivatives thereof include methyl vinyl ether. Vinyl amines and derivatives thereof include dimethylaminoethyl (meth)acrylate, diethylaminoethyl (meth)acrylate, diisopropylaminoethyl (meth)acrylate, mono-t-butylaminoethyl (meth)acrylate, morpholinoethyl(meth)acrylate and monomers which can be post-reacted to form amine groups, such as vinyl formamide. Vinyl aryl amines and derivatives thereof include vinyl aniline, vinyl pyridine, N-vinyl carbazole and vinyl imidazole. Vinyl nitriles and derivatives thereof include (meth)acrylonitrile. Vinyl ketones and derivatives thereof include acreolin.

Hydroxyl-containing monomers include vinyl hydroxyl monomers such as hydroxyethyl (meth)acrylate, hydroxy propyl (meth)acrylate, glycerol mono(meth)acrylate and sugar mono(meth)acrylates such as glucose mono(meth) acrylate. Monomers which can be post-reacted to form hydroxyl groups include vinyl acetate, acetoxystyrene and glycidyl (meth)acrylate. Acid-containing or acid functional monomers include (meth)acrylic acid, styrene sulfonic acid, vinyl phosphoric acid, vinyl benzoic acid, maleic acid, fumaric acid, itaconic acid, 2-(meth)acrylamido 2-ethyl propanesulfonic acid, mono-2-((meth)acryloyloxy)ethyl succinate and ammonium sulfatoethyl (meth)acrylate. Zwitterionic monomers include (meth)acryloyl oxyethylphosphoryl choline and betaines, such as [2-((meth)acryloyloxy)ethyl] dimethyl-(3-sulfopropyl)ammonium hydroxide. Quatemised amino monomers include (meth)acryloyloxyethyltri-(alklaryl)ammonium halides such as (meth) acryloyloxyethyltrimethyl ammonium chloride.

Oligomeric (or polymeric) monomers include oligomeric (meth)acrylic acid esters such as mono(alk/aryl)oxyoligoalkyleneoxide(meth)acrylates and mono(alk/aryl)o xyoligodimethyl-siloxane(meth)acrylates. These esters include monomethoxy oligo(ethyleneglycol) mono(meth)acrylate, monomethoxy oligo(propyleneglycol) mono(meth)acrylate, monohydroxy oligo(ethyleneglycol) mono(meth)acrylate and monohydroxy oligo(propyleneglycol) mono(meth)acrylate.

Further examples include vinyl or allyl esters, amides or ethers of pre-formed oligomers formed via ring-opening polymerisation such as oligo(caprolactam) or oligo-(caprolactone), or oligomers formed via a living polymerisation technique such as oligo(1,4-butadiene). The polymeric monomers are the same, save that the oligomers are polymers.

Macromonomers are generally formed by linking a polymerisable moiety, such as a vinyl or allyl group, to a pre-formed monofunctional polymer via a suitable linking unit such as an ester, an amide or an ether. Examples of suitable polymers include mono functional poly(alkylene oxide) such as monomethoxy[poly(ethyleneoxide) or monomethoxy [poly-(propyleneoxide), silicones such as poly(dimethylsiloxane), polymers formed by ring-opening polymerisation such as poly(caprolactone) or poly(caprolactam) or mono-functional polymers formed via living polymerisation such as poly(1,4-butadiene).

Preferred macromonomers include monomethoxy[poly-(ethyleneglycol)] mono (methacrylate), monomethoxy [poly-(propyleneglycol)] mono(methacrylate), poly (dimethylsiloxane) monomethacrylate.

The corresponding allyl monomers to those listed above can also be used where appropriate.

More preferred monomers include: amide-containing monomers such as (meth)acrylamide, N,N'-dimethyl(meth)acrylamide, N and or N'-di(alkyl or aryl) (meth)acrylamide, N-vinyl pyrollidone, (meth)acrylamidopropyl trimethyl ammonium chloride, [3-(methacroylamino) propyl]dimethyl ammonium chloride, 3-[N-(3-methacrylamido-propyl)-N,N-dimethyl]-aminopropane sulfonate, 4-(2-acrylamido-2-methylpropyl-dimethylammonio) butanoate, methyl acrylamidoglycolate methyl ether and N-isopropyl-(meth)acrylamide; (meth)acrylic acid derivatives such as (meth)acrylic acid, (meth)acryoloyl chloride (or any halide), (alkyl/aryl) (meth)acrylate, oligo-functionalised monomers such as monomethoxy polyethyleneglycol) monomethacrylate or monomethoxy poly(propyleneglycol) mono(meth) acrylate, glycerol mono(meth)acrylate, glycidyl (meth)acrylate and sugar mono(meth)acrylates such as glucose mono (meth)acrylate; vinyl amines such as dimethylaminoethyl (meth)acrylate, diethylaminoethyl (meth)acrylate, t-butylamino (meth)acrylate, morpholinoethylmethacrylate, or vinyl aryl amines such as vinyl aniline, vinyl pyridine, N-vinyl carbazole, vinyl imidazole; vinyl aryl monomers such as styrene, vinyl benzyl chloride, vinyl toluene, α-methyl styrene, styrene sulfonic acid and vinyl benzoic acid; vinyl hydroxyl monomers such as hydroxyethyl (meth) acrylate, hydroxy propyl (meth)acrylate, glyceryl (meth) acrylate or monomers which can be post-functionalised into hydroxyl groups such as vinyl acetate or acetoxy styrene can also be used; acid-containing monomers such as (meth) acrylic acid, styrene sulfonic acid, vinyl phosphonic, maleic acid, fumaric acid, itaconic acid, 2-acrylamido 2-ethyl propanesulfonic acid and mono-2-(methacryloyloxy)ethyll succinate. Cr aryl/alkyl esters thereof. Or carboxylic anhydride containing monomers such as maleic anhydride; zwitterionic monomers such as (meth)acryloyloxyethyl-phosphoryl choline, quaternised amino monomers such as methacryloyloxyethyltrimethyl ammonium chloride.

The corresponding allyl monomer, where applicable, can also be use in each case.

Hydrophobic monomers include: vinyl aryl compounds such as styrene and vinylbenzyl chloride; (meth)acrylic acid esters such as mono-t-butylaminoethyl (meth)acrylate, C1-20 alkyl(meth)acrylates (linear & branched), aryl(meth) acrylates such as benzyl methacrylate; oligomeric (meth) acrylic acid esters such as mono(alk/aryl)oxyoligo-[dimethylsiloxane (meth)acrylate] and tri(alkyloxy)-silylalkyl (meth)acrylates such as trimethoxysilylpropyl-(meth)acrylate.

Functional monomers, i.e. monomers with reactive pendant groups which can be post or pre-modified with another moiety can also be used such as glycidyl (meth)acrylate, trimethoxysilylpropyl(meth)acrylate, (meth)acryloyl chloride, maleic anhydride, hydroxyalkyl (meth)acrylates, (meth)acrylic acid, vinylbenzyl chloride, activated esters of (meth)acrylic acid such as N-hydroxysuccinamido (meth) acrylate and acetoxystyrene.

The copolymer may contain unreacted polymerisable groups from the multifunctional monomer.

Especially preferred monomers for chain growth polymerisation are: $C_1$-$C_{20}$ linear or branched, alkyl, alkaryl or aryl acrylates and methacrylates.

Ratio of Step-Growth to Chain Growth Polymer:

The weight fraction of step growth polymer in the combined step growth and chain growth polymers comprising the particle is typically 10% to 99%, preferably 15% to 80%, more preferably 25% to 75%.

Cross-Linking Agents for Chain-Growth Polymerisation:

Cross-linking agents can be used to modify the properties of the chain-growth polymer. Suitable materials comprise a molecule containing at least two vinyl groups that may be polymerised. The molecule may be hydrophilic, hydrophobic, amphiphilic, neutral, cationic, zwitterionic or oligomeric. Examples include di- or multivinyl esters, di- or multivinyl amides, di- or multivinyl aryl compounds and di- or multivinyl alk/aryl ethers. Typically, in the case of oligomeric or multifunctional branching agents, a linking reaction is used to attach a polymerisable moiety to a di- or multifunctional oligomer or a di- or multifunctional group. The brancher may itself have more than one branching point, such as 'T'-shaped divinylic oligomers. In some cases, more than one multifunctional monomer may be used.

Macro cross-linkers or macro branchers (multifunctional monomers typically having a molecular weight of at least 1000 Daltons) are generally formed by linking a polymerisable moiety, such as a vinyl or aryl group, to a pre-formed multifunctional polymer via a suitable linking unit such as an ester, an amide or an ether. Examples of suitable polymers include di-functional poly(alkylene oxides) such as poly (ethyleneglycol) or polypropylene glycol), silicones such as poly(dimethyl-siloxane)s, polymers formed by ring-opening polymerisation such as poly(caprolactone) or poly(caprolactam) or poly-functional polymers formed via living polymerisation such as poly(1,4-butadiene).

Preferred macro branchers include poly(ethyleneglycol) di(meth)acrylate, poly(propyleneglycol) di(meth)acrylate, (meth)acryloxypropyl-terminated poly (dimethylsiloxane), poly(caprolactone) di(meth)acrylate and poly(caprolactam) di(meth)acrylamide.

The corresponding allyl monomers to those listed above can also be used where appropriate.

Preferred multifunctional monomers include but are not limited to divinyl aryl monomers such as divinyl benzene; (meth)acrylate diesters such as glycerol di(meth)acrylate, ethylene glycol di(meth)acrylate, propyleneglycol di(meth) acrylate and 1,3-butylenedi(meth)acrylate; oligoalkylene oxide di(meth)acrylates such as tetra ethyleneglycol di(meth)acrylate, oligo(ethyleneglycol) di(meth)acrylate and oligo(propyleneglycol) di(meth)-acrylate; divinyl acrylamides such as methylene bis-acrylamide; silicone-containing divinyl esters or amides such as (meth)acryloxypropyl-terminated oligo (dimethyl-siloxane); divinyl ethers such as oligo (ethyleneglycol)-divinyl ether; and tetra- or tri-(meth)acrylate esters such as pentaerythritol tetra-(meth)acrylate, trimethylolpropane tri(meth)acrylate or glucose di- to penta (meth)acrylate. Further examples include vinyl or allyl esters, amides or ethers of pre formed oligomers formed via ring-opening polymerisation such as oligo(caprolactam) or oligo-(caprolactone), or oligomers formed via a living polymerisation technique such as oligo(1,4-butadiene).

Especially preferred cross-linkers are divinyl benzene, ethylene glycol di(meth)acrylate and trimethylolpropane tri (meth)acrylate.

Levels of cross-linker are typically 0-75, preferably 0.0001 to 50, more preferably 0.0001 to 25 mol %.

Benefit Agents:

Various benefit agents can be incorporated into the particles. Where the end use of the particles is in connection with a surfactant-containing system, any compatible benefit agent which can provide a benefit to a substrate which is treated with a surfactant composition can be used. Preferred benefit agents are in the laundry field, for example fabric benefit agents, and benefit agents which provide a benefit to a laundry wash and/or rinse medium. In the alternative benefit agents may provide a skin or hair related benefit. Advantages of the particles of the invention in the presence of surfactant are a good retention of the benefit agent on storage of a formulation and controllable release of the benefit agent during and after product usage.

Preferred examples include flavours and fragrances, enzymes, antifoams, fluorescer, shading dyes and/or pigments, conditioning agents (for example water-insoluble quaternary ammonium materials and/or silicones), sunscreens, ceramides, antioxidants, reducing agents, sequestrants, colour care additives, density matching polymers, photo-bleaches, lubricants, unsaturated oils, emollients/moisturiser and antimicrobial agents.

Preferred antimicrobials include Triclosan™, climbazole, octapyrox, ketoconizole, zinc pyrithione, and quaternary ammonium compounds.

Preferred sunscreens and/or skin lightening agents are vitamin B3 compounds. Suitable vitamin B3 compounds are selected from niacin, niacinamide, nicotinyl alcohol, or derivatives or salts thereof. Other vitamins which act as skin lightening agents can be advantageously included in the skin lightening composition to provide for additional skin lightening effects. These include vitamin B6, vitamin C, vitamin A or their precursors. Mixtures of the vitamins can also be employed in the composition of the invention. An especially preferred additional vitamin is vitamin B6. Other non-limiting examples of skin lightening agents useful herein include adapalene, aloe extract, ammonium lactate, arbutin, azelaic acid, butyl hydroxy anisole, butyl hydroxy toluene, citrate esters, deoxyarbutin, 1,3 diphenyl propane derivatives, 2,5 di hydroxylbenzoic acid and its derivatives, 2-(4-acetoxyphenyl)-1,3 dithane, Hydroxylphenyl)-1,3 dithane, ellagic acid, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, 2,4 resorcinol derivatives, 3,5 resorcinol derivatives, salicylic acid, 3,4,5 trihydroxybenzyl derivatives, and mixtures thereof. Preferred sunscreens useful in the present invention are 2-ethylhexyl-p-methoxycinnamate, butyl methoxy dibenzoylmethane, 2-hydroxy-4-methoxybenzophenone, octyl dimethyl-p-aminobenzoic acid and mixtures thereof. Particularly preferred sunscreen is chosen from 2-ethyl hexyl-p-methoxycinnamate, 4,-t-butyl-4'-methoxydibenzoyl-methane or mixtures thereof. Other conventional sunscreen agents that are suitable for use in the skin lightening composition of the invention include 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexyl-salicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonic benzoxazoic acid and mixtures of these compounds.

Preferred anti-oxidants include vitamin E, retinol, antioxiants based on hydroxytoluene such as Irganox™ or commercially available antioxidants such as the Trollox™ series.

Perfume and fragrance materials (which include pro-fragrances) are a particularly preferred benefit agent.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damscenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil. Perfume components which are odiferous materials are described in further detail below.

The perfume is typically present in an amount of from 10-85% by total weight of the particle, preferably from 15 to 75% by total weight of the particle. The perfume suitably has a molecular weight of from 50 to 500 Dalton. Pro-fragrances can be of higher molecular weight, being typically 1-10 kD.

Useful components of the perfume include materials of both natural and synthetic origin. They include single compounds and mixtures. Specific examples of such components may be found in the current literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well known top-notes include citrus oils, linalool, linalyl acetate, lavender, dihydromyrcenol, rose oxide and cis-3-hexanol. Top notes typically comprise 15-25% wt of a perfume composition and in those embodiments of the invention which contain an increased level of top-notes it is envisaged at that least 20% wt would be present within the particle.

Typical perfume components which it is advantageous to employ in the embodiments of the present iuvention include those with a relatively low boiling point, preferably those with a boiling point of less than 300, preferably 100-250 Celsius.

It is also advantageous to encapsulate perfume components which have a low Log P (i.e. those which will be partitioned into water), preferably with a Log P of less than 3.0. These materials, of relatively low boiling point and relatively low Log P have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benzyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and for Viridine It is commonplace for a plurality of perfume components to be present in a formulation. In the encapsulates of the present invention it is envisaged that there will be four or more, preferably five or more, more preferably six or more or even seven or more different perfume components from the list given of delayed blooming perfumes given above present in the particles.

Another group of perfumes with which the present invention can be applied are the so-called 'aromatherapy' materials. These include many components also used in perfumery, including components of essential oils such as Clary Sage, Eucalyptus, Geranium, Lavender, Mace Extract, Neroli, Nutmeg, Spearmint, Sweet Violet Leaf and Valerian. By means of the present invention these materials can be transferred to textile articles that will be worn or otherwise come into contact with the human body (such as handkerchiefs and bed linen).

Surface Modifications and Deposition Aids:

Surface modifications, including deposition aids modify the properties of the exterior of the particle. One particular benefit which can be obtained with these materials is to make the particle more substantive to a desired substrate. Desired substrates include cellulosics (including cotton), polyesters (including those employed in the manufacture of polyester fabrics) and protein-containing substrates (such as akin and hair). Deposition aids are preferably selected from non-hydrolysable cotton-substantive polymers, hydrolysable cotton-substantive polymers and polyester-substantive polymers.

Preferred polysaccharide polymers, whether hydrolysable or not may be derived from a broad range of polysaccharides. Preferably, the polysaccharide is selected from the group consisting of: tamarind gum (preferably consisting of xyloglucan polymers), guar gum, locust bean gum (preferably consisting of galactomannan polymers), and other industrial gums and polymers, which include, but are not limited to, Tara, Fenugreek, Aloe, Chia, Flaxseed, Psyllium seed, quince seed, xanthan, gellan, welan, rhamsan, dextran, curdlan, pullulan, scleroglucan, schizophyllan, chitin, hydroxyalkyl cellulose, arabinan (preferably from sugar beets), de-branched arabinan (preferably from sugar beets), arabinoxylan (preferably from rye and wheat flour), galactan (preferably from lupin and potatoes), pectic galactan (preferably from potatoes), galactomannan (preferably from carob, and including both low and high viscosities), glucomannan, lichenan (preferably from icelandic moss), mannan (preferably from ivory nuts), pachyman, rhamnogalacturonan, acacia gum, agar, alginates, carrageenan, chitosan, clavan, hyaluronic acid, heparin, inulin, cellodextrins, cellulose, cellulose derivatives and mixtures thereof.

Preferred non-hydrolysable cotton-substantive deposition aids include non-hydrolysable polysaccharides. The polysaccharide preferably has a β-1,4-linked backbone.

Preferably the polysaccharide is a cellulose, a cellulose derivative, or another β-1,4-linked polysaccharide having an affinity for cellulose, such as polymannan, polyglucan, polyglucomannan, polyxyloglucan and polygalactomannan or a mixture thereof. More preferably, the polysaccharide is selected from the group consisting of polyxyloglucan and polygalactomannan. Most preferably, the deposition aid is locust bean gum, xyloglucan, guar gum or mixtures thereof.

Preferred hydrolysable cotton-substantive deposition aids include hydrolysable polysaccharides. These comprise a polysaccharide which has been modified to render it more water soluble by means of a group covalently attached to the polysaccharide by means of hydrolysable bond. Preferred groups may for example be independently selected from one or more of acetate, propanoate, trifluoroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Preferred amongst such hydrolysable deposition aids is cellulose mono acetate.

Suitable and preferred polyester-substantive deposition aids include phthalate containing polymers, more preferably a polymer having one or more nonionic hydrophilic components comprising oxyethylene, polyoxyethylene, oxypropylene or polyoxypropylene segments, and, one or more hydrophobic components comprising terephthalate segments. Typically, oxyalkylene segments of these deposition aids will have a degree of polymerization of from 1 to about 400, although higher levels can be used, preferably from 100 to about 350, more preferably from 200 to about 300.

One type of preferred deposition aid is a copolymer having random blocks of ethylene terephthalate and polyethylene oxide terephthalate.

Another preferred polymeric deposition aid is polyester with repeat units of ethylene terephthalate units contains 10-15% by weight of ethylene terephthalate units together with 90-80% by weight of polyoxyethylene terephthalate units, derived from a polyethylene glycol of average molecular weight 0.2 kD-40 kD. Examples of this class of polymer include the commercially available material ZELCON 5126 (from DuPont) and MILEASE T (from ICI). Examples of related polymers can be found in U.S. Pat. No. 4,702,857.

Another preferred polymeric deposition aid is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451. Other suitable polymeric soil release agents include the terephthalate polyesters of U.S. Pat. No. 4,711,730, the anionic end-capped oligomeric esters of U.S. Pat. No. 4,721,580, and the block polyester oligomeric compounds of U.S. Pat. No. 4,702,857.

Preferred polymeric deposition aids also include the soil release agents of U.S. Pat. No. 4,877,896 which discloses anionic, especially sulfoarolyl, end-capped terephthalate esters.

Still another preferred deposition aid is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred deposition aid of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

The deposition aid may be straight or branched. The preferred molecular weight of the polymeric deposition aid is in the range of from about 5 kD to about 500 kD, preferably 10 kD-500 kD, more preferably 20 kD-300 kD.

Preferably, the deposition-aid polymer is present at levels such that the ratio polymer:particle solids is in the range 1:500-3:1, preferably 1:200-1:3.

Preparation Methods

Polymerisation occurs in at least two phases. In an earlier of these phases a shell is formed by a step-growth polymerisation. This shell encloses and contains the reagents for the chain-growth reaction which occurs in a later phase.

Temporal separation of these phases is accomplished by control of the reagents present and the reaction conditions.

Typically, at least one of the components of the shell-forming reaction is withheld from the initial reaction mixture and added gradually to control the progress of the reaction in the first phase.

Advantageously, the first phase of the reaction is performed under conditions in which the chain-growth reaction is inhibited. These conditions include a sufficiently low temperature (for a thermally activated reaction) or conditions of sufficiently low light (for a photo-activated reaction).

Once the shell-forming reaction has proceeded sufficiently, the conditions are modified (for example, by raising the temperature or exposing the reaction mixture to light) to cause the reaction to form the inner region to start.

The preferred method is one in which an emulsion is formed comprising the chain-growth polymer components in a non-aqueous dispersed phase and the step-growth polymer components are at the interface between the dispersed phase and the continuous aqueous phase.

Typically the aqueous phase comprises an emulsifying agent, and one of the co-monomers for the step-growth polymer. It may also contain any diol, alcohol or amine cross-linking agent.

The disperse phase comprises the chain-growth monomer, the initiator, any isocyanate or vinyl cross-linking agents, the other co-monomer for the step growth polymer and any optional benefit agent.

The benefit agent may be present in the reaction mixture, at a level to give the benefit agent levels in the resulting particles at the levels disclosed above, although it is also possible to form "empty" particles and subsequently expose them to a benefit agent which can be adsorbed into the inner region.

Surface modification materials are generally added to the aqueous phase towards the end of the process, where, for example, further monomer(s) can be added to form further shell material and bind additional materials to the outside of the particle.

Emulsifying Agents

Many emulsifying agents are known for use in emulsion polymerisation. Suitable emulsifying agents for use in the polymerisation process may comprise, but are not limited to, non-ionic surfactants such as polyvinylpyrrolidone (PVP), polyethylene glycol sorbitan monolaurate (Tween 20), polyethylene glycol sorbitan monopalmitate (tween 40), polyethylene glycol sorbitan monooleate (Tween 80), polyvinyl alcohol (PVA), and poly(ethoxy)nonyl phenol, ethylene maleic anhydride (EMA) copolymer, Easy-Sperse™ (from ISP Technologies Inc.), ionic surfactants such as partially neutralized salts of polyacrylic acids such as sodium or potassium polyacrylate or sodium or potassium polymethacrylate. Brij™-35, Hypermer™ A 60, or sodium lignosulphate, and mixtures thereof.

Emulsifiers may also include, but are not limited to, acrylic acid-alkyl acrylate copolymer, poly(acrylic acid), polyoxyalkylene sorbitan fatty esters, polyalkylene co-carboxy anhydrides, polyalkylene co-maleic anhydrides, poly (methyl vinyl ether-co-maleic anhydride), polypropylene-co-maleic anhydride), poly(butadiene co-maleic anhydride), and polyvinyl acetate-co-maleic anhydride), polyvinyl alcohols, polyalkylene glycols, polyoxyalkylene glycols, and mixtures thereof.

Preferred emulsifying agents are fatty alcohol exthoylates (particularly of the Brij™ class), salts of ether sulphates (including SLES), alkyl and alkaryl sulphonates and sulphates (including LAS and SDS) and cationic quaternary salts (including CTAC and CTAB).

It is particularly preferred that the emulsifying agent comprises a nonionic surfactant. This is believed to produce a particle which deposits better on cloth than one produced soley with an anionic surfactant emulsifier, as cloth become anionic during a wash. It is also preferred that the non-ionic surfactant is hydrophilic, so as to promote the formation of a stable mini-emulsion. The alcohol ethoxylates with more than ten moles of ethoxylation, for example Synperonic A20 (C1320EO), yield good results. DLS data for samples shows that as the level of surfactant increases the particle size becomes smaller, which is also advantageous. Preferably, the ratio of non-ionic to anionic emulsifier should be greater than 1:1 (i.e. non-ionic is present in excess) and the total surfactant level should be >3% wt of the polymerisation mixture.

Co-Surfactant:

Typically a co-surfactant will be present in the dispersed phase and in the resulting particle. Suitable co-surfactants for use in the present invention include hexadecane, cetyl alcohol, lauroyl peroxide, n-dodecyl mercaptan, dodecyl methacrylate, stearyl methacrylate, polystyrene, polydecene, mineral oils, isopropyl myristate $C_{13}$-$C_{15}$ alkyl benzoate and polymethyl methacrylate.

The preferred cosurfactants comprise hexadecane, polydecene and isopropyl myristate.

As a wt % of oil phase as a total, the co-surfactant is typically 0-20%, preferably 1-15%, more pref 2-12.5%.

Catalyst

Optional catalyst may be present in the dispersed phase of the emulsion. This advantageously minimises the hydrolysis of isocyanate to primary amine, which can react with further isocyanate to form polyurea. This unwanted reaction can result in an excess of diol being left at the end of the process which can potentially lead to the formation of malodour and interfere with cross-linking reactions.

Suitable catalysts may comprise amino or organo-metalic compounds such as N,N'-dimethylaminoethanol, N,N'-dimethylcyclohexylamine, bis-(2-dimethylaminoethyl)ether, N,N'-dimethylacetylamine, diaminobicyclooctane, stannous octoate and dibutyl tin dilaurate, 1,3-bis(dimethylamino) butane, pentamethyldiethylenetriamine and mixtures thereof.

The level of catalyst is typically 0.1-2% with respect to chain-growth monomer.

Polymerisation Conditions

As noted above, polymerisation typically occurs in at least two phases. In the earlier phase the shell is preferably formed by a reaction which, in preferred embodiments occurs at less than about 60 Celsius, typically 15-55 Celsius. In the later phase the inner region is polymerised at a preferred temperature of more than about 70 Celcius, typically 70-95 Celcius.

Both reactions are allowed to proceed for sufficiently long for polymerisation to be essentially complete, 1-3 hours being typical for each stage.

Deposition aid may added at the end of the later phase (preferably after cooling), when for example, further shell forming material (for example further isocyanate and co-momomer) are also added to bind the deposition aid to the outer surface of the particle by the formation of further shell material which entraps a portion of the deposition aid and leads to a "hairy" particle in which the "hair" comprises the deposition aid.

For simple core-shell particles, the core excluding benefit agent is less than or equal to 80% wt of mass, and the shell generally 20% wt or greater of the mass of the particle.

Preferably the emulsion polymerisation step is a so-called "mini-emulsion" polymerisation, performed with a dispersed phase droplet size of below one micron. Sufficiently fine emulsions can be obtained by a range of methods, including sonication, and/or via high shear dynamic mixers or static mixers. Mini-emulsion products have excellent suspending properties.

Formaldehyde Scavenger:

Compositions including the particles of present invention can comprise (if required) a formaldehyde scavenger. The formaldehyde scavengers disclosed in EP 1797947 can be used in embodiments of the invention. In the alternative a formaldehyde scavenger can be added at the end of polymerisation to the aqueous phase of the reaction mixture.

The formaldehyde scavengers of the present invention are preferably selected from beta-dicarbonyl compounds, mono- or di-amide materials, amines and other materials which can react with formaldehyde and remove it.

Suitable beta-dicarbonyl compounds of the present have an acidic hydrogen giving rise to a nucleophilic attack on formaldehyde.

Preferred beta-dicarbonyl compounds are acetoacetamide (BKB (available in the marketplace from Eastman)), ethyl acetoacetate (EAA (available in the marketplace from Eastman)), N,N-Dimethyleneacetamide (DMAA (available in the marketplace from Eastman)), acetoacetone, dimethyl-1,3-acetonedicarboxylate, 1,3-acetonedicarboxylic acid, malonic acid, resorcinol, 1,3-cyclohexadione, barbituric acid, 5,5-dimethyl-1,3-cyclohexanedione (dimedone), 2,2-dimethyl-1,3-dioxane-4,6-dione (Meldrum's acid), salicylic acid, methyl acetoacetate (MAA (available in the marketplace from Eastman)), ethyl-2-methyl acetoacetate, 3-methyl-acetoacetone, dimethyl malonate, diethyl malonate, 1,3-dimethyl barbituric acid, resorcinol, phloroglucinol, orcinol, 2,4-dihydroxy benzoic acid, 3,5-dihydroxy benzoic acid, and malonamide. Other suitable beta-dicarbonyl scavenger are listed in U.S. Pat. Nos. 5,194,674 and 5,446,195 as well as in Tomasino et al, Textile Chemist and Colorist, vol. 16, No. 12 (1984), Mono or Di-amides may also be used as effective formaldehyde scavengers.

Examples of the preferred effective mono- and di-amide scavengers are urea, ethylene urea, propylene urea, caprolactam, glycouril, hydantoin, 2-oxazolidinone, 2-pyrrolidinone, uracil, barbituric acid, thymine, uric acid, allantoin, polyamides, 4,5-dihydroxyethylene urea, monomethylol-4-hydroxy-4-methoxy-5,5-dimethyl-propylurea, nylon 2-hydroxyethyl ethylene urea (SR-511; SR-512 (Sartomer)), 2-hydroxyethyl urea (Hydrovance (National Starch)), L-citrulline, biotin, N-methyl urea, N-ethyl urea, N-butyl urea, N-phenyl urea, 4,5-dimethoxy ethylene urea and succinimide.

Another class of compounds that are effective formaldehyde scavengers are amines which form imines by reaction with formaldehyde.

Preferred amines include, poly(vinyl amine) (Lupamin™ (BASF)), arginine, lysine, asparagines, proline, tryptophan, 2-amino-2-methyl-1-propanol (AMP); proteins such as casein, gelatin, collagen, whey protein, soy protein, and albumin; melamine, benzoguanamine, 4-aminobenzoic acid (PABA), 3-aminobenzoic acid, 2-aminobenzoic acid (anthranilic acid), 2-aminophenol, 3-aminophenol, 4-aminophenol, creatine, 4-aminosalicylic acid, 5-aminosalicylic acid, methyl anthranilate, methoxyamine HCl, anthranilamide, 4-aminobenzamide, p-toluidine, p-anisidine, sulfanilic acid, sulfanilamide, methyl-4-aminobenzoate, ethyl-4-aminobenzoate (benzocain), beta-diethylaminoethyl-4-aminobenzoate (procain), 4-aminobenzamide, 3,5-diaminobenzoic acid and 2,4-diaminophenol.

Other amines as disclosed in copending U.S. Letters for patent application Ser. No. 11/123,898 and U.S. Pat. No. 6,261,483, and in Tomasino et al, Textile Chemist and Colorist, vol. 16, No. 12 (1984).

Other formaldehyde scavengers are known, for example, hydrazines such as 2,4-dinitrophenylhydrazine react with formaldehyde to give hydrazones. The reaction is pH-dependent and reversible. Other preferred amines can be selected from a non-limiting list of 1,2-phenylenediamine, 1,3-phenylenediamine, and 1,4-phenylenediamine.

In addition, aromatic amines, triamines, and aliphatic polyamine may also be used. Examples of these amines may include, but are not limited to, aniline, hexamethylenediamine, bis-hexamethylenetriamine, triethyl-aminetriamine, poly(propyleneoxide) triamine, and poly(propyleneglycol)-diamines.

The formaldehyde scavengers of WO 2007/091223 may also be used in embodiments of the invention. These are sodium bisulfite, urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzo-guanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), poly(vinyl amine), hexane diol, ethylenediamine-N,N'-bisacetoacetamide, N-(2-ethylhexyl)acetoacetamide, N-(3-phenylpropyl) acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, benzylamine, hydroxycitronellol, cyclohexanone, 2-butanone, pentane dione, dehydroacetic acid, chitosan, and/or mixtures thereof.

Particularly preferred scavengers comprise at least one of urea, ethylene urea, ethylacetamide, acetoacetamide and mixtures thereof. The most preferred scavengers are selected from the group consisting of urea, ethylene urea, ethylacetamide, acetoacetamide and mixtures thereof.

Particularly Preferred Embodiments

The invention most preferably subsists in a particle having an average diameter of less than 50 micron comprising:
a) at least one polyurethane shell;
b) interior to said shell, a solid core formed by chain growth polymerisation of ethylenically unsaturated species, preferably comprising acrylates and/or methacrylates.

It is particularly preferred that the above particle comprises a fragrance absorbed in the core, and/or a polysaccharide deposition aid exterior to the shell. Especially preferred particles have a particle size of 50-500 nm. As will be described in further detail below, the particles find particularly advantageous application in compositions which are intended for the treatment of the surface of skin, hair or laundry where the deposition aid is selected such that it is substantive to the surface being treated.

Use in Products

The end-product compositions of the invention may be in any physical form e.g. a solid such as a powder or granules, a tablet, a solid bar, a paste, gel or liquid, especially, an aqueous-based liquid.

The particles of the invention may be advantageously incorporated into surfactant-containing and, in particular laundry and personal care compositions. The particles are typically included in said compositions at levels of from 0.001% to 10%, preferably from 0.005% to 7.55%, most preferably from 0.01% to 5% by weight of the total composition.

For laundry applications, one active ingredient in the compositions is preferably a surface active agent or a fabric conditioning agent. More than one active ingredient may be included. For some applications a mixture of active ingredients may be used.

Formulated compositions comprising the particles of the invention may contain a surface-active compound (surfactant) which may be chosen from soap and non soap anionic, cationic, non-ionic, amphoteric and zwitterionic surface active compounds and mixtures thereof. Many suitable surface active compounds are available and are fully described in the literature, for example, in "Surface-Active Agents and Detergents", Volumes I and II, by Schwartz, Perry and Berch. The preferred surface-active compounds that can be used are soaps and synthetic non soap anionic, and non-ionic compounds.

The compositions of the invention may contain linear alkylbenzene sulphonate, particularly linear alkylbenzene sulphonates having an alkyl chain length of from C8 to C15. It is preferred if the level of linear alkylbenzene sulphonate is from 0 wt % to 30 wt %, more preferably from 1 wt % to 25 wt %, most preferably from 2 wt % to 15 wt %, by weight of the total composition.

Compositions may contain other anionic surfactants in amounts additional to the percentages quoted above. Suitable anionic surfactants are well-known to those skilled in the art. Examples include primary and secondary alkyl sulphates, particularly C8 to C15 primary alkyl sulphates; alkyl ether sulphates; olefin sulphonates; alkyl xylene sulphonates; dialkyl sulphosuccinates; and fatty acid ester sulphonates. Sodium salts are generally preferred.

Compositions may also contain non-ionic surfactant. Nonionic surfactants that may be used include the primary and secondary alcohol ethoxylates, especially the C8 to C20 aliphatic alcohols ethoxylated with an average of from 1 to 20 moles of ethylene oxide per mole of alcohol, and more especially the C10 to C15 primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %, by weight of a fully formulated composition comprising the particles of the invention.

Any conventional fabric conditioning agent may be used. The conditioning agents may be cationic or non-ionic. If the fabric conditioning compound is to be employed in a main wash detergent composition the compound will typically be non-ionic. For use in the rinse phase, typically they will be cationic. They may for example be used in amounts from 0.5% to 35%, preferably from 1% to 30% more preferably from 3% to 25% by weight of a fully formulated composition comprising the particles of the invention.

Suitable cationic fabric softening compounds are substantially water-insoluble quaternary ammonium materials comprising a single alkyl or alkenyl long chain having an average chain length greater than or equal to C20 or, more preferably, compounds comprising a polar head group and two alkyl or alkenyl chains having an average chain length greater than or equal to C14. Preferably the fabric softening compounds have two long chain alkyl or alkenyl chains each having an average chain length greater than or equal to C16. Most preferably at least 50% of the long chain alkyl or alkenyl groups have a chain length of C18 or above. It is preferred if the long chain alkyl or alkenyl groups of the fabric softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surfactants Science Series" volume 34 ed. Richmond 1990, volume 37 ed. Rubingh 1991 and volume 53 eds. Cross and Singer 1994, Marcel Dekker Inc. New York".

The fabric softening compounds are preferably compounds that provide excellent softening, and are characterised by a chain melting $L\beta$ to $L\alpha$ transition temperature greater than 25 Celsius, preferably greater than 35 Celsius, most preferably greater than 45 Celsius. This $L\beta$ to $L\alpha$ transition can be measured by differential scanning calorimetry as defined in "Handbook of Lipid Bilayers", D Marsh, CRC Press, Boca Raton, Fla., 1990 (pages 137 and 337).

Substantially water-insoluble fabric softening compounds are defined as fabric softening compounds having a solubility of less than $1 \times 10^{-3}$ wt % in demineralised water at 20 Celsius. Preferably the fabric softening compounds have a solubility of less than $1 \times 10^{-4}$ wt %, more preferably from less than $1 \times 10^{-8}$ to $1 \times 10^{-6}$ wt %.

Especially preferred are cationic fabric softening compounds that are water-insoluble quaternary ammonium materials having two C12-22 alkyl or alkenyl groups connected to the molecule via at least one ester link, preferably two ester links. Di(tallowoxyloxyethyl) dimethyl ammonium chloride and/or its hardened tallow analogue is an especially preferred compound of this class.

A second preferred type comprises those derived from triethanolamine (hereinafter referred to as 'TEA quats') as described in for example U.S. Pat. No. 3,915,867. Suitable materials are, for example, N-methyl-N,N,N-triethanolamine ditallowester or di-hardened-tallowester quaternary ammonium chloride or methosulphate. Examples of commercially available TEA quats include Rewoquat WE18 and Rewoquat WE20, both partially unsaturated (ex. WITCO), Tetranyl AOT-1, fully saturated (ex. ICAO) and Stepantex VP 85, fully saturated (ex. Stepan).

It is advantageous if the quaternary ammonium material is biologically biodegradable.

It is also possible to include certain mono-alkyl cationic surfactants which can be used in main-wash compositions for fabrics. Cationic surfactants that may be used include quaternary ammonium salts of the general formula $R_1R_2R_3R_4N^+ X^-$ wherein the R groups are long or short hydrocarbon chains, typically alkyl, hydroxyalkyl or ethoxylated alkyl groups, and X is a counter-ion (for example, compounds in which R1 is a C8-C22 alkyl group, preferably a C8-C10 or C12-C14 alkyl group, R2 is a methyl group, and R3 and R4, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for hand-washing products and for products intended for use in different types of washing machine.

The total amount of surfactant present will also depend on the intended end use and may, in fully formulated products, be as high as 60 wt %, for example, in a composition for washing fabrics by hand. In compositions for machine washing of fabrics, an amount of from 5 to 40 wt % is generally appropriate. Typically compositions will comprise at least 2 wt % surfactant e.g. 2-60%, preferably 15-40% most preferably 25-35%, by weight.

Detergent compositions suitable for use in most automatic fabric washing machines generally contain anionic non-soap surfactant, or non-ionic surfactant, or combinations of the two in any suitable ratio, optionally together with soap. Compositions, when used as main wash fabric washing compositions, will generally also contain one or more detergency builders. The total amount of detergency builder in compositions will typically range from 5 to 80 wt %, preferably from 10 to 60 wt %, by weight of composition. Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions of the invention preferably contain an alkali metal, preferably sodium, aluminosilicate builder. Sodium aluminosilicates may generally be incorporated in end product formulations amounts of from 10 to 70% by weight (anhydrous basis), preferably from 25 to 50 wt %.

The alkali metal aluminosilicate may be either crystalline or amorphous or mixtures thereof, having the general formula: 0.8 1.5 Na2O. Al2O3. 0.8 6 SiO2

These materials contain some bound water and are required to have a calcium ion exchange capacity of at least 50 mg CaO/g. The preferred sodium aluminosilicates contain 1.5 3.5 SiO2 units (in the formula above). Both the amorphous and the crystalline materials can be prepared readily by reaction between sodium silicate and sodium aluminate, as amply described in the literature. Suitable crystalline sodium aluminosilicate ion exchange detergency builders are described, for example, in GB 1 429 143 (Procter & Gamble). The preferred sodium aluminosilicates of this type are the well known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium weight ratio not exceeding 1.33, preferably within the range of from 0.90 to 1.33, and more preferably within the range of from 0.90 to 1.20.

Especially preferred is zeolite MAP having a silicon to aluminium weight ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono, di¬ and trisuccinates, carboxymethyloxy succinates, carboxymethyloxymalonates, dipicolinates, hydroxyethyliminodiacetates, alkyl and alkenylmalonates and succinates; and sulphonated fatty acid salts. This list is not intended to be exhaustive.

Especially preferred organic builders are citrates, suitably used in fully formulated compositions in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions comprising particles according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in a fully formulated product in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N', N', tetracetyl ethylenediamine (TAED) and sodium nonanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. Examples of such peracids can be found in U.S. Pat. No. 4,686,063 and U.S. Pat. No. 5,397,501 (Unilever). A preferred example is the imido peroxycarboxylic class of peracids described in EP A 325 288, EP A 349 940, DE 382 3172 and EP 325 289. A particularly preferred example is phthalimido peroxy caproic acid (PAP). Such peracids are suitably present at 0.1-12% wt, preferably 0.5-10% wt.

A bleach stabiliser (transition metal sequestrant) may also be present in fully formulated products. Suitable bleach stabilisers include ethylenediamine tetra-acetate (EDTA), the polyphosphonates such as Dequest (Trade Mark) and non phosphate stabilisers such as EDDS (ethylene diamine di succinic acid). These bleach stabilisers are also useful for stain removal especially in end-products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

Advantageously in the compositions of the invention benefit agents, particularly, perfume components may be employed which are sensitive to bleaches as the encapsulation of, for example, the perfume component within the particles will provide some degree of protection to the perfume component or other benefit agent.

The fully formulated compositions may also contain one or more enzyme(s).

Suitable enzymes include the proteases, amylases, cellulases, oxidases, peroxidases and lipases usable for incorporation in detergent compositions. Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4-12 are available and can be used in the instant invention. Examples of suitable proteolytic enzymes are the subtilisins which are obtained from particular strains of *B. Subtilis B. licheniformis*, such as the commercially available subtilisins Maxatase (Trade Mark), as supplied by Genencor International N.V., Delft, Holland, and Alcalase (Trade Mark), as supplied by Novozymes Industri A/S, Copenhagen, Denmark.

Particularly suitable is a protease obtained from a strain of *Bacillus* having maximum activity throughout the pH range of 8-12, being commercially available, e.g. from Novozymes Industri A/S under the registered trade names Esperase (Trade Mark) and Savinase (Trade Mark). The preparation of these and analogous enzymes is described in GB 1 243 785. Other commercial proteases are Kazusase (Trade Mark obtainable from Showa Denko of Japan), Optimase (Trade Mark from Miles Kali Chemie, Hannover, West Germany), and Superase (Trade Mark obtainable from Pfizer of U.S.A.).

Detergency enzymes are commonly employed in fully formulated products in granular form in amounts of from about 0.1 to about 3.0 wt % on product. However, any suitable physical form of enzyme may be used. Advantageously in the compositions of the invention benefit agents, for example, perfume components, may be employed which are sensitive to enzymes as the encapsulation of the perfume component (or other benefit agent) within the particles will provide some degree of protection to the perfume component (or other benefit agent).

The compositions of the invention may contain alkali metal, preferably sodium carbonate, in order to increase detergency and ease processing. Sodium carbonate may suitably be present in fully formulated products in amounts ranging from 1 to 60 wt %, preferably from 2 to 40 wt %. However, compositions containing little or no sodium carbonate are also within the scope of the invention.

The fully formulated detergent composition when diluted in the wash liquor (during a typical wash cycle) will typically give a pH of the wash liquor from 7 to 10.5 for a main wash detergent.

Particulate detergent compositions are suitably prepared by spray drying a slurry of compatible heat insensitive ingredients, and then spraying on or post-dosing those ingredients unsuitable for processing via the slurry. The skilled detergent formulator will have no difficulty in deciding which ingredients should be included in the slurry and which should not. It is particularly useful to add the perfume particles of the present invention via post-dosing.

Particulate detergent compositions preferably have a bulk density of at least 400 g/liter, more preferably at least 500 g/liter. Especially preferred compositions have bulk densities of at least 650 g/liter, more preferably at least 700 g/liter.

Such powders may be prepared either by post tower densification of spray dried powder, or by wholly non tower methods such as dry mixing and granulation; in both cases a high-speed mixer/granulator may advantageously be used. Processes using high speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

As noted above the particles of the present invention are particularly suited to processes for manufacture of products which feature "late variant addition" of benefit agents (particularly of perfume).

In order that the present invention may be still further understood and carried forth into practice it will be further described with reference to the following examples:

EXAMPLES

General

Benefit Agent

Perfumes tend to be complex mixtures of molecules. For the purpose of these examples, a simplified and reproducible model perfume was used unless otherwise stated. The model perfume is split into three compositions relating to top, middle and base notes.

Top Note Perfume Composition:

| Component | Cas No. | Wt % | ClogP | MW | Mass/g |
|---|---|---|---|---|---|
| melon valerate | 39255-32-8 | 20 | 2.411 | 153 | 144.21 |
| Aldehyde C8 | 124-13-0 | 20 | 2.765 |  | 128.21 |
| Tetra hydro Linalol | 78-69-3 | 20 | 3.241 | 220 | 158.28 |
| benzyl acetate | 140-11-4 | 20 | 1.604 | 214 | 150.17 |
| Linalyl Acetate | 115-95-7 | 20 | 3.114 | 220 | 196.29 |

Middle Note Perfume Composition:

| Component | Cas No. | Wt % | ClogP | MW | Mass/g |
|---|---|---|---|---|---|
| OTBCA | 88-41-5 | 35 | 3.112 |  | 198.30 |
| damascone, delta | 57378-68-4 | 5 | 3.387 | 267 | 192.30 |
| aldehyde c12 | 112-54-9 | 20 | 4.59 | 223 | 184.32 |
| verdyl acetate | 5413-60-5 | 20 | 1.766 | 175 | 192.25 |
| ionone beta | 14901-07-6 | 20 | 3.355 |  | 192.30 |

Base Note Perfume Composition:

| Component | Cas No. | Wt % | ClogP | MW | Mass/g |
|---|---|---|---|---|---|
| bangalol | 28219-61-6 | 20 | 3.728 |  | 208.34 |
| iso E super (OTNE) | 54464-57-2 | 20 | 4.138 |  | 234.38 |
| hexyl cinnamic aldehyde | 101-86-0 | 20 | 4.677 |  | 216.32 |
| cyclopentadecanolide | 106-02-5 | 20 | 5.294 | 303 | 240.38 |
| phenyl ethyl 2 phenylacetate | 102-20-5 | 20 | 3.624 | 324 | 240.30 |

Particle Preparation

A general procedure was followed for all mini-emulsion synthesis; a typical example is as follows.

1. The following were combined in a 30 ml vial:
   Poly(phenyl isocyanate) (3.86 g)—cross-linker for step-growth polymerisation;

isophorone diisocyanate (8.05 g)—co-monomer for step-growth polymerisation;
top note perfume (32 g)—benefit agent (when present);
dibutyl tin dilaurate (0.088 g)—catalyst;
hexadecane (1.23 g)—co-surfactant;
methyl methacrylate (8.32 g)—monomer for chain-growth polymerisation;
2,2'-azobisisobutyronitrile (0.083 g)—free-radical initiator for chain-growth polymerisation;

2. The following were dissolved in 67.1 g water and cooled to below 10° C.:
Sodium dodecyl sulphate (1.23 g)—emulsifier;
1,1,1-tris(hydroxymethyl)propane (1.52 g)—cross-linker for step-growth polymer 1,6-hexane diol (4.28 g)—co-monomer for step-growth polymerisation;

3. Using a sonic probe, the two phases obtained at (1) and (2) were mixed for three minutes whilst cooled in an ice bath.

4. The mini-emulsion solution resulting from step (3) was placed in a round bottom flask and stirred at an external temperature of 55° C. and 200 rpm for three hours.

5. After three hours the temperature was increased to 85° C. and the reaction stirred for a further two hours.

6. After five hours the reaction was cooled and decanted.

The reaction vessel and stirrer should be checked for signs of coagulation and grit formation. Final solids content was determined by gravimetric analysis.

Procedure for Cotton Deposition Aid Grafting:

P 1. Prepare 1% LBG/Xyloglucan by dissolving 1 g poly (saccharide) in 99 g boiling water by stirring with a homogeniser at 12,000 rpm for 2 minutes.

2. Weigh 100 g of 20% solids (mini)emulsion particles into round bottom flask.

3. To this, add 20 g of poly(saccharide) stock solution.

4. Attach an overhead stirrer and condenser and heat to 80° C.

5. After the mixture has been stirred at 350 rpm for 1 hour add ascorbic acid (0.096 g in 1 ml water) and methyl acrylate (1.01 g)

6. Allow the mixture to stir for 2 minutes before adding 30% hydrogen peroxide solution (0.275 g)

7. After 90 minutes add a further portion of ascorbic acid (0.032 in 0.5 ml water) and 30% hydrogen peroxide (0.09 g)

8. Once the reaction has finished (3-4 h) allow the reaction to cool, and transfer to a labelled jar.

Procedure for Polyester Deposition Aid Grafting:

1. Prepare 1% PET-POET by dissolving 1 g polymer in 99 g boiling water by Stirring with a homogenises at 12,000 rpm for 2 minutes.

2. Weigh 100 g of 20% solids (mini)emulsion particle into round bottom flask.

3. To this, add 20 g of poly(saccharide) stock solution.

4. Attach an overhead stirrer and condenser and heat to 80° C. for 1 hour.

5. Cool the reaction back to 25° C.

6. Add dropwise over five minutes isophorone diisocyanate (2.17 g) and dibutyltindilaurate (0.03 g) and stir for a further 55 minutes.

7. Add 1,6-hexanediol (1.16 g) dissolved in water (1.65 g) and heat to 80° C. and stir for two hours 8. Once the reaction has finished (4-5 h) allow the reaction to cool, and transfer to a labelled jar.

Washing Experiments:

In washing experiments particle deposition was measured by turbidity as follows:

a) Preparation of Stock Solutions:
   Surfactant Stock: (10 g/L 50:50 LAS:A7) was prepared by dissolving Linear Alkyl Benzene Sulphonate (9.09 g LAS (55% Active)) and Synperonic A7 (5 g) in de-ionised water to a total of 1 liter.
   Base Buffer Stock: (0.1 M) was prepared by dissolving Sodium Carbonate (7.5465 g) and Sodium Hydrogen Carbonate (2.4195 g) in de-ionised water to a total of 1 liter.

b) Preparation of the Wash Liquor:
   Base Buffer Stock (10 ml) and surfactant stock (10 ml) were added to a 500 ml Linitest pot and 80 ml de-ionised water was added to produce a wash liquor buffered at pH 10.5 and containing 1 g/L surfactant (50:50 LAS:A7).

c) Simulated Wash:
   0.04 g (400 ppm on wash liquor) of polymer particles: Unmodified capsules were each added to the linitest pots containing wash liquor and agitated slightly to ensure mixing. Washes were done in duplicate for each sample and results averaged. A 5 ml aliquot was taken from each and the Absorbance at 400 nm recorded using a 1 cm cuvette. This absorbance value represents 100% particles in the wash solution prior to the simulated simulated wash process.

d) Linitest Equipment and Procedure:
   A section of unfluoresced cotton (or knitted polyester as appropriate) measuring 20 cm by 20 cm was placed into each linitest pot containing the wash liquor and polymer particles and the pot was sealed.

The Linitest™ is a laboratory scale washing machine (Ex. Heraeus). The equipment is designed and built to comply with the requirements for international standard test specifications. It is used for small scale detergency and stain removal testing particularly when low liquor to cloth ratios are required.

There are various models of the Linitest commercially available. The model used in this case has a single rotation speed of 40 rpm. The carrier is capable of accommodating twelve 500 ml steel containers and can be operated at temperatures up to 100° C.

The Linitest comprises a 20 liter tank, control system and drive mechanism. Permanent thermostatically controlled tubular heating elements in the base of the tank heat the bath liquor to the required temperature. The stainless steel construction throughout ensures efficient heat transfer to the specimen containers that are mounted on a rotating horizontal carrier driven by a geared motor. The rotating movement of the carrier 'throws' the liquid from one end of the container to the other in a continuous action. This movement simulates the mechanical washing process and additional mechanical action can be obtained by using steel ball bearings or discs.

The Linitest pots were attached to the Linitester cradle and rotated 45 minutes at 40° C. to simulate the main wash.

The cloths were then removed and wrung by hand and a 5 ml aliquot of the remaining wash liquor was taken and the absorbance at 400 nm measured using a 1 cm cuvette as before. From interpolation of the initial calibration curve, the concentration of the particles remaining the liquor after the wash could be determined and hence the level deposited (wash deposition) on the cloth could be determined by difference.

The Linitest pots were then thoroughly rinsed and the 'wrung' cloths returned to the pots and 125 ml of de-ionised water was added. The Linitester bath water was drained and the pots attached to the cradle and rotated for 10 minutes at ambient temperature (~20° C.) to simulate a rinse procedure. The clothes were then removed and wrung by hand. A 5 ml aliquot of the rinse solution was taken and the absorbance at 400 nm determined. As before interpolation of the initial calibration plot allowed the particle concentration removed from the cloth during the rinse to be determined and by comparison to the initial level deposited prior to the rinse, the percentage loss from the cloth could be determined. This procedure was repeated a further two times to simulate and determine losses from the second and third rinse.

In the following examples, all quantities are given in grams unless otherwise specified. Perfume retention within the particles is determined by placing the particles in a model laundry detergent formulation and determining the proportion of the perfume that remains free after an elapsed time. Decrease in perfume content in the surfactant base was determined by a colorimetric assay.

Example 1: Poly(Urethane) Miniemulsion Synthesis with Various Cross-Linker Levels (Prior Art)

| Experiment | 1 | 2 | 3 | 4 | 5 | 6 | 7 |
|---|---|---|---|---|---|---|---|
| X-Linker Level | 1 | 2 | 4 | 8 | 16 | 32 | 0 |
| Poly(phenyl isocyanate) | 0.133 | 0.266 | 0.534 | 1.071 | 2.155 | 4.360 | 0 |
| Isophorone diisocyanate | 12.936 | 12.815 | 12.571 | 12.082 | 11.095 | 9.087 | 13.057 |
| Dibutyltin dilaurate | 0.088 | 0.088 | 0.088 | 0.088 | 0.088 | 0.088 | 0.088 |
| Hexadecane | 0.82 | 0.82 | 0.82 | 0.82 | 0.82 | 0.82 | 0.82 |
| Sodium dodecyl sulphate | 0.82 | 0.82 | 0.82 | 0.82 | 0.82 | 0.82 | 0.82 |
| 1,1,1-tris (hydroxyl-methyl) propane | 0.053 | 0.105 | 0.211 | 0.423 | 0.850 | 1.721 | 0 |
| 1,6-Hexane diol | 6.878 | 6.813 | 6.684 | 6.424 | 5.899 | 4.831 | 6.942 |
| Water | 78.3 | 78.3 | 78.3 | 78.3 | 78.3 | 78.3 | 78.3 |

The level of cross-linker refers to the percentage of isocyanate, or hydroxyl groups, on a tri-functional molecule, i.e. poly(phenyl isocyanate) or 1,1,1-tris(hydroxyl-methyl) propane. The remainder is present on a difunctional, chain extending molecule, i.e. isophorone diisocyanate or 1,6-hexane diol.

The materials prepared were added into a non-concentrated laundry liquid base which contained 0.75% top-note perfume at 2% solids. The materials were then analysed after 1, 5 and 8 days to determine how much perfume had been absorbed into the particle. A blank measurement was taken to ensure no response from the particle itself and a T=0 measurement was prepared by adding water to the base instead of mini-emulsion particles.

The non cross-linked particle (example 1.7) adsorbed very little perfume. A general increase in perfume absorption was observed with increasing cross-linker level. At the highest cross-linker levels around 35% of the perfume has been adsorbed.

| Experiment | 1 | 2 | 3 | 4 | 5 | 6 | 7 |
|---|---|---|---|---|---|---|---|
| X-Linker Level | 1 | 2 | 4 | 8 | 16 | 32 | 0 |
| Free perfume at T = 0 | 100% | 100% | 100% | 100% | 100% | 100% | 100% |
| Free perfume at T = 1 day | 77.8 | 73.6 | 73.9 | 72.4 | 64.3 | 66.6 | 98.2 |
| Free perfume at T = 5 days | 75.9 | 72.2 | 71.9 | 79.3 | 59.2 | 59.8 | 95.19 |
| Free perfume at T = 8 days | 79.9 | 75.1 | 78.8 | 73.5 | 67.4 | 66.1 | 97.6 |

Example 2: Poly(Urethane) Hybrid Mini-Emulsion Synthesis with Various Cross-Linker Levels and Various Monomers

| Experiment | 8 | 9 | 10 | 11 | 12 | 13 |
|---|---|---|---|---|---|---|
| poly(phenyl isocyanate) | 0.264 | 0.264 | 0.264 | 0.264 | 0.264 | 0.264 |
| Isophorone Diisocyanate | 12.692 | 12.692 | 12.692 | 12.692 | 12.692 | 12.692 |

-continued

| | | | | | | |
|---|---|---|---|---|---|---|
| Butyl Acrylate (BA) | 9.093 | | | | | |
| Ethyl hexyl methacrylate (EHMA) | | 9.093 | | | | |
| Butyl Methacrylate (BMA) | | | 9.093 | | | |
| Methyl Methacrylate (MMA) | | | | 9.093 | | |
| Methyl Acrylate (MA) | | | | | 9.093 | |
| Styrene (STY) | | | | | | 9.093 |
| AIBN | 0.091 | 0.091 | 0.091 | 0.091 | 0.091 | 0.091 |
| Dibutyltindilaurate | 0.096 | 0.096 | 0.096 | 0.096 | 0.096 | 0.096 |
| Hexadecane | 1.344 | 1.344 | 1.344 | 1.344 | 1.344 | 1.344 |
| SDS | 1.23 | 1.23 | 1.23 | 1.23 | 1.23 | 1.23 |

-continued

| | | | | | | |
|---|---|---|---|---|---|---|
| 1,6-Hexane Diol | 6.748 | 6.748 | 6.748 | 6.748 | 6.748 | 6.748 |
| 1,1,1-Tris (hydroxyl-methyl) propane | 0.104 | 0.104 | 0.104 | 0.104 | 0.104 | 0.104 |
| Water | 68.65 | 68.65 | 68.65 | 68.65 | 68.65 | 68.65 |
| Experiment | 14 | 15 | 16 | 17 | 18 | 19 |
| poly(phenyl isocyanate) | 4.226 | 4.226 | 4.226 | 4.226 | 4.226 | 4.226 |
| Isophorone Diisocyanate | 8.807 | 8.807 | 8.807 | 8.807 | 8.807 | 8.807 |
| Butyl Acrylate (BA) | 9.093 | | | | | |

-continued

| | | | | | | |
|---|---|---|---|---|---|---|
| Ethyl hexyl methacrylate (EHMA) | | 9.093 | | | | |
| Butyl Methacrylate (BMA) | | | 9.093 | | | |
| Methyl Methacrylate (MMA) | | | | 9.093 | | |
| Methyl Acrylate (MA) | | | | | 9.093 | |
| Styrene (STY) | | | | | | 9.093 |
| AIBN | 0.091 | 0.091 | 0.091 | 0.091 | 0.091 | 0.091 |
| Dibutyltindilaurate | 0.096 | 0.096 | 0.096 | 0.096 | 0.096 | 0.096 |
| Hexadecane | 1.344 | 1.344 | 1.344 | 1.344 | 1.344 | 1.344 |
| SDS | 1.344 | 1.344 | 1.344 | 1.344 | 1.344 | 1.344 |
| 1,6-Hexane Diol | 4.682 | 4.682 | 4.682 | 4.682 | 4.682 | 4.682 |
| 1,1,1-Tris (hydroxyl-methyl) propane | 1.668 | 1.668 | 1.668 | 1.668 | 1.668 | 1.668 |
| Water | 68.65 | 68.65 | 68.65 | 68.65 | 68.65 | 68.65 |

A range of samples according to the invention at two crosslinker levers (2% and 32%) were prepared using a selection of different free radical monomers as given in the tables above.

The materials prepared were added into a non-concentrated laundry liquid base which contained 0.75% top note perfume at 2% solids. The materials were then analysed after 1, 5 and 8 days to determine how much perfume had been absorbed into the particle. A blank measurement was taken to ensure no response from the particle itself and a T=0 measurement was prepared by adding water to the base instead of particles.

Higher crosslink density samples absorbed typically 20 to 30 percent more fragrance. Initially this result appeared surprising as it would be expected that a highly cross-linked particle would be difficult for the fragrance to penetrate. However given that the leakage mechanism from these materials is thermodynamically controlled rather than kinetically controlled, the level of free perfume should be the same from an encapsulated perfume as is it is from a system starting with free perfume and dosed with an identical empty particle.

| Experiment | 8 | 14 | 9 | 15 | 10 |
|---|---|---|---|---|---|
| X-linker Level | 2% | 32% | 2% | 32% | 2% |
| Core Monomer | BA | BA | EHMA | EHMA | BMA |
| Free perfume at T = 0 | 100 | 100 | 100 | 100 | 100 |
| Free perfume at T = 1 day | 40.6 | 26.1 | 35.6 | 11.1 | 52.6 |
| Free perfume at T = 5 days | 38.1 | 28.2 | 33.4 | 10.8 | 53.0 |
| Free perfume at T = 8 days | 41.3 | 29.4 | 37.7 | 13.4 | 52.4 |

| Experiment | 16 | 11 | 17 | 13 | 19 |
|---|---|---|---|---|---|
| X-linker Level | 32% | 2% | 32% | 2% | 32% |
| Core Monomer | BMA | MMA | MMA | STY | STY |
| Free perfume at T = 0 | 100 | 100 | 100 | 100 | 100 |
| Free perfume at T = 1 day | 24.9 | 58.24 | 35.0 | 68.1 | 45.6 |
| Free perfume at T = 5 days | 19.18 | 62.1 | 24.3 | 64.6 | 41.8 |
| Free perfume at T = 8 days | 25.9 | 65.08 | 37.6 | 61.9 | 46.4 |

In example 1, the particles are purely a poly-urethane step-growth polymer without a separate core material and are formed by formed interfacial polymerisation. In this example 2, the core, formed by a chain growth polymerisation is also present. Comparing the results of example 2 with example 1, it can be seen that much lower levels of free perfume are left unadsorbed with the particles comprising a core.

Leakage can be compared with the solubility parameter value for the core monomer. The lower the solubility parameter difference value (Delta SP) the more compatible the fragrance is with the core monomer. This will lead to a lower level of free perfume and hence a lower colorimetric response when an assay is conducted. This will translate to a lower absorption value. A correlation can be found between solubility parameter and free fragrance.

The lowest solubility parameter value materials show the lowest level of free perfume and conversely the highest solubility parameter materials the highest level of free perfume.

Looking only at the higher level of cross-linker, it is possible to see that the solubility parameters of the core vary with the monomer used. The table below shows the effect of varying the nature of the core monomer on the solubility parameter.

| Monomer | Delta_SP | % Free Perfume |
|---|---|---|
| EHA | 1.19 | 11.8 |
| BMA | 1.78 | 23.3 |
| BA | 2.23 | 27.9 |

| Monomer | Delta_SP | % Free Perfume |
|---|---|---|
| MMA | 3.89 | 32.3 |
| STY | 7.28 | 44.6 |

The level of the perfume in the particles can be assumed to be 100% minus the level of free perfume. Thus it can be seen that the acrylate core monomers performed better than the styrene.

Example 3: Poly(Urethane) Hybrid Miniemulsion Synthesis with Various Monomers and Various Ratios of Poly(Urethane) to Free Radical Polymer

| Experiment | 20 | 21 | 22 | 23 | 24 | 25 |
|---|---|---|---|---|---|---|
| poly(phenyl isocyanate) | 5.866 | 5.233 | 4.579 | 3.925 | 3.270 | 2.616 |
| Isophorone Diisocyanate | 12.268 | 10.904 | 9.542 | 8.179 | 6.816 | 5.452 |
| Butyl Methacrylate (BMA) | 3 | 6 | 9 | 12 | 15 | 18 |
| AIBN | 0.083 | 0.083 | 0.083 | 0.083 | 0.083 | 0.083 |
| Dibutyltindilaurate | 0.088 | 0.088 | 0.088 | 0.088 | 0.088 | 0.088 |
| Hexadecane | 1.23 | 1.23 | 1.23 | 1.23 | 1.23 | 1.23 |
| SDS | 1.23 | 1.23 | 1.23 | 1.23 | 1.23 | 1.23 |
| 1,6-Hexane Diol | 6.522 | 5.798 | 5.073 | 4.348 | 3.623 | 2.899 |
| 1,1,1-Tris(hydroxymethyl)propane | 2.323 | 2.065 | 1.807 | 1.549 | 1.290 | 1.032 |
| Water | 67.12 | 67.12 | 67.12 | 67.12 | 67.12 | 67.12 |

| Experiment | 26 | 27 | 28 | 29 | 30 | 31 |
|---|---|---|---|---|---|---|
| poly(phenyl isocyanate) | 5.233 | 3.925 | 2.616 | 5.233 | 3.925 | 2.616 |
| Isophorone Diisocyanate | 10.905 | 8.179 | 5.452 | 10.905 | 8.179 | 5.452 |
| Ethylhexyl Methacrylate (EHMA) | 6 | 12 | 18 | | | |
| Methyl Methacrylate (MMA) | | | | 6 | 12 | 18 |
| AIBN | 0.083 | 0.083 | 0.083 | 0.083 | 0.083 | 0.083 |
| Dibutyltindilaurate | 0.08 | 0.088 | 0.088 | 0.088 | 0.088 | 0.088 |
| Hexadecane | 1.23 | 1.23 | 1.23 | 1.23 | 1.23 | 1.23 |
| SDS | 1.23 | 1.23 | 1.23 | 1.23 | 1.23 | 1.23 |
| 1,6-Hexane Diol | 5.798 | 4.348 | 2.899 | 5.798 | 4.348 | 2.899 |
| 1,1,1-Tris(hydroxymethyl)propane | 2.065 | 1.549 | 1.032 | 2.065 | 1.549 | 1.032 |
| Water | 67.12 | 67.12 | 67.12 | 67.12 | 67.12 | 67.12 |

Example 3 shows how it it is possible to vary the ratio of the chain growth (free radical) core and the step-growth (poly(urethane)) shell in the hybrid particle. This will affect the level of fragrance that can be absorbed into the core. This example shows the effect on perfume absorption from varying the level of a butyl methacrylate (BMA) present.

| Experiment | 20 | 21 | 22 | 23 | 24 | 25 |
|---|---|---|---|---|---|---|
| Step Growth: Chain Growth (shell:core) | 90:10 | 80:20 | 70:30 | 60:40 | 50:50 | 40:60 |
| Core Monomer | BMA | BMA | BMA | BMA | BMA | BMA |
| Free perfume at T = 0 | 100 | 100 | 100 | 100 | 100 | 100 |
| Free perfume at T = 1 day | 25.8 | 21.0 | 22.7 | 13.6 | 9.9 | 8.3 |
| Free perfume at T = 5 days | 32.4 | 22.9 | 22.3 | 14.3 | 11.5 | 11.1 |
| Free perfume at T = 8 days | 33.0 | 21.2 | 21.7 | 15.9 | 12.5 | 11.9 |
| Average Free Perfume | 30.4 | 21.7 | 22.2 | 14.6 | 11.3 | 10.4 |

| Experiment | 26 | 27 | 28 | 29 | 30 | 31 |
|---|---|---|---|---|---|---|
| Step Growth: Chain Growth (shell:core) | 80:20 | 40:60 | 60:40 | 80:20 | 40:60 | 60:40 |
| Core Monomer | EHMA | EHMA | EHMA | MMA | MMA | MMA |
| Free perfume at T = 0 | 100 | 100 | 100 | 100 | 100 | 100 |
| Free perfume at T = 1 day | 9.3 | 6.3 | 6.1 | 29.9 | 17.4 | 22.2 |
| Free perfume at T = 5 days | 14.5 | 10.9 | 7.9 | 38.3 | 22.9 | 18.1 |
| Free perfume at T = 8 days | 12.5 | 12.9 | 7.9 | 41.4 | 24.9 | 16.8 |
| Average Free Perfume | 12.1 | 10.0 | 7.3 | 36.5 | 21.7 | 19.0 |

As with the previous example the deficit of free perfume has been adsorbed into the particles. It can be seen that as the level of shell material is proportionately reduced the amount of perfume being adsorbed increases.

Example 4: Poly(Urethane) Hybrid Mini-Emulsion Synthesis with Butyl Methacrylate Core Cross-Linked at Various Levels

| Experiment | 32 | 33 | 34 | 35 | 36 | 37 |
|---|---|---|---|---|---|---|
| poly(phenyl isocyanate) | 3.270 | 3.270 | 3.270 | 3.270 | 3.270 | 3.270 |
| Isophorone Diisocyanate | 6.816 | 6.816 | 6.816 | 6.816 | 6.816 | 6.816 |
| BMA | 15 | 14.925 | 14.85 | 14.7 | 14.4 | 13.8 |
| 1,3 Butanediol Dimethacrylate | 0.0 | 0.075 | 0.15 | 0.3 | 0.6 | 1.2 |
| AIBN | 0.083 | 0.083 | 0.083 | 0.083 | 0.083 | 0.083 |
| Dibutyltindi-laurate | 0.088 | 0.088 | 0.088 | 0.088 | 0.088 | 0.088 |
| Hexadecane | 1.23 | 1.23 | 1.23 | 1.23 | 1.23 | 1.23 |
| SDS | 1.23 | 1.23 | 1.23 | 1.23 | 1.23 | 1.23 |
| 1,6-Hexane Diol | 3.623 | 3.623 | 3.623 | 3.623 | 3.623 | 3.623 |
| 1,1,1-Tris (hydroxymethyl) propane | 1.290 | 1.290 | 1.290 | 1.290 | 1.290 | 1.290 |
| Water | 67.12 | 67.12 | 67.12 | 67.12 | 67.12 | 67.12 |

The results suggest that the addition of cross-linker to the core does not affect perfume absorption at levels up to two mol percent. When increasing from two to eight mol percent the level of free perfume is doubled, indicating that the particle is less able to adsorb perfume.

| Experiment | 32 | 33 | 34 | 35 | 36 | 37 |
|---|---|---|---|---|---|---|
| Core X-linker Level | 0% | 0.5% | 1% | 2% | 4% | 8% |
| Free perfume at T = 0 | 100 | 100 | 100 | 100 | 100 | 100 |
| Free perfume at T = 1 day | 20.5 | 15.1 | 18.3 | 16.9 | 21.5 | 31.0 |
| Free perfume at T = 5 days | 17.5 | 15.3 | 16.5 | 14.4 | 19.7 | 31.4 |
| Free perfume at T = 8 days | 17.2 | 14.9 | 16.3 | 14.6 | 19.8 | 37.3 |
| Average Free Perfume | 18.4 | 15.1 | 17.0 | 15.3 | 20.3 | 33.2 |

These results also show how an equilibrium between the free perfume and the perfume in the particles is rapidly established. Over 60% of the added perfume has been adsorbed into the particles after the first day.

Example 5: Addition of Deposition Aid

Methyl acrylate was used as a monomer for grafting deposition aids, due to its rate of initiation, propagation and water solubility are best suited for this purpose. A poly(urethane) condensation polymerisation reaction was used to graft a PET-POET polymer to a poly(urethane) shell This was achieved by first adding a solution of PET-POET to the encapsulate slurry to allow the polymer to physically absorb onto the encapsulates. The PET-POET was then permanently attached via the addition of isocyanate and diol.

| Sample | Poly(urethane) particle (no deposition aid) | Poly(urethane) particle + PET-POET |
|---|---|---|
| Deposition after wash | 1.7% | 43.0% |
| Deposition after rinse 1 | 1.5% | 39.8% |
| Deposition after rinse 2 | 1.6% | 34.1% |

The results clearly show that with the deposition aid the deposition of the particles onto substrate was significantly increased.

Example 6: Incorporated Benefit Agent

| Sample | 38 | 39 | 40 | 41 | 42 | 43 |
|---|---|---|---|---|---|---|
| poly(phenyl isocyanate) | 3.86 | 3.86 | 3.86 | 3.86 | 3.86 | 3.86 |
| Isophorone Diisocyanate | 8.05 | 8.05 | 8.05 | 8.05 | 8.05 | 8.05 |
| Perfume | 3.2 | 3.2 | 3.2 | 3.2 | 3.2 | 3.2 |
| Ethyl hexyl acrylate | 8.32 | | | | | |
| Ethyl hexyl methacrylate | | 8.32 | | | | |
| Butyl Methacrylate | | | 8.32 | | | |
| Benzyl Methacrylate | | | | 8.32 | | |
| Methyl Acrylate | | | | | 8.32 | |
| Styrene | | | | | | 8.32 |
| AIBN | 0.08 | 0.08 | 0.08 | 0.08 | 0.08 | 0.08 |
| Dibutyltindi-laurate | 0.08 | 0.08 | 0.08 | 0.08 | 0.06 | 0.08 |
| Hexadecane | 1.23 | 1.23 | 1.23 | 1.23 | 1.23 | 1.23 |
| Synperonic A20 | 1.50 | 1.50 | 1.50 | 1.50 | 1.50 | 1.50 |
| SDS | 0.38 | 0.38 | 0.38 | 0.38 | 0.38 | 0.38 |
| 1,6-Hexane Diol | 4.28 | 4.28 | 4.28 | 4.28 | 4.28 | 4.28 |
| 1,1,1-Tris (hydroxymethyl) propane | 1.53 | 1.53 | 1.53 | 1.53 | 1.53 | 1.53 |
| Water | 67.13 | 67.13 | 67.13 | 67.13 | 67.13 | 67.13 |

A range of samples according to the invention at two crosslinker levers (2% and 32%) were prepared using a selection of different free radical monomers as given in the tables above.

The materials prepared were added into a non-concentrated laundry liquid base which at 5% solids and hence a perfume level of 0.5% in the liquid base. The materials were then analysed after 1, 5 and 8 days to determine how much perfume had been leaked from the particle into the base.

| Experiment | 41 | 40 | 39 | 38 |
|---|---|---|---|---|
| Core Monomer | BzMA | BMA | EHMA | EHA |
| Free perfume at T = 1 day | 22.5 | 12.7 | 7.4 | 6.0 |
| Free perfume at T = 5 days | 22.4 | 12.9 | 8.9 | 6.6 |
| Free perfume at T = 8 days | 21.0 | 14.1 | 8.1 | 5.5 |

Leakage can be compared with the solubility parameter value for the core monomer. The lower the solubility parameter difference value (Delta SP) the more compatible the fragrance is with the core monomer. This will lead to a lower level of free perfume and hence a lower colorimetric response when an assay is conducted. This will translate to a lower leakage value. A correlation can be found between solubility parameter and free fragrance.

The lowest solubility parameter value materials show the lowest level of free perfume and conversely the highest solubility parameter materials the highest level of free perfume.

| Monomer | Delta_SP | % Free Perfume (Average) |
|---------|----------|--------------------------|
| BzMA    | 2.27     | 22.0                     |
| BMA     | 1.77     | 13.3                     |
| EHMA    | 1.27     | 8.2                      |
| EHA     | 1.19     | 6.0                      |

The invention claimed is:

1. A method of forming a particle comprising:
   a) reacting at least one step-growth monomer and at least one first cross-linking agent in a step-growth polymerization reaction to form at least one shell of the particle, wherein the first cross-linking agent is 2-35 mol % of the step-growth monomer; and
   b) after step a), reacting at least one chain-growth monomer, at least one second cross-linking agent in a chain-growth polymerisation reaction to form an inner region of the particle, wherein the chain-growth polymerisation reaction does not involve an isocyanate,
      (i) wherein the at least one second cross-linking agent is 0.0001-25 mol % of the at least one chain-growth monomer,
      (ii) wherein the particle has an average diameter of less than 500 nm;
      (iii) wherein the particle has a perfume in the inner region of the particle;
      (iv) wherein the particle has a deposition aid exterior of the at least one shell of the particle, and
      (v) wherein the particle is configured to adsorb over 60% of the perfume into the particle after one day.

2. The method according to claim 1, wherein the step-growth polymerisation reaction is not condensation polymerisation.

3. The method according to claim 1, wherein the chain-growth polymerisation reaction is a radical polymerisation reaction.

4. The method according to claim 1, further comprising: decorating a surface of the particle with a deposition aid comprising a polysaccharide;
   wherein the deposition aid is substantive to proteinaceous, cellulosic, polyester or polyamide surfaces.

5. The method according to claim 1, wherein the benefit agent comprises a hydrophobic benefit agent.

6. A method comprising;
   a) providing an emulsion having a mean dispersed particle size diameter of less than 500 nm and having
      (1) a dispersed non-aqueous phase comprising:
         i) a first co-monomer, capable of step-growth polymerization with a suitable second co-monomer;
         (ii) a first cross-linking agent that is 2-35 mol % of the first co-monomer;
         iii) a benefit agent, wherein the non-aqueous phase is configured to adsorb over 60% of an amount of the benefit agent after one day;
         iv) at least one monomer capable of chain-growth polymerization;
         (v) a second cross-linking agent that is 0.0001-25 mol % of the at least one monomer; and,
         vi) a radical initiator which is not significantly active at the temperature at which the first and second co-monomer undergoes step-growth polymerization;
      (2) and, a continuous aqueous phase comprising:
         i) water,
         ii) emulsifying agent,
         iii) a second co-monomer
   b) maintaining the emulsion at a temperature at which the step-growth polymerisation occurs but not the chain growth polymerisation,
   c) maintaining the emulsion at a temperature at which the chain-growth polymerisation proceeds, and
   d) adding a deposition aid after step (c).

7. The method according to claim 6, wherein the at least one monomer capable of chain growth polymerisation comprises an ethylenically unsaturated vinyllic monomer.

8. The method according to claim 1, wherein the particle further comprises at least one cross-linking agent, derived from at least one of:
   i) a more than di-functional agent having isocyanate, alcohol, or amine functionality, or
   ii) a more than mono-functional vinyllic monomer.

9. The method of claim 1 further comprising:
   forming a plurality of particles according to steps a) and b):
   dispersing the plurality of particles in a composition;
   wherein the composition is at least one of a laundry detergent, laundry conditioner, deodorant, antiperspirant, shampoo, hair conditioner or skin care or skin cleansing product.

10. The method of preparing the composition according to claim 9, wherein the particles and the benefit agent are added separately so as to result in the particles taking up the benefit agent in the composition.

11. The method of claim 2, wherein the step-growth polymerisation reaction involves an isocyanate monomer.

12. The method of claim 2, wherein the step-growth polymerisation reaction involves at least one of urethane or urea.

13. The method of claim 3, wherein the radical polymerisation reaction of at least one ethylenically unsaturated vinyllic monomer.

14. The method of claim 3, wherein the radical polymerisation reaction of at least one of acrylate or methacryate.

15. The method of claim 5, wherein the hydrophobic benefit agent comprises an organoleptic benefit agent.

16. The method of claim 5, wherein the hydrophobic benefit agent comprises a flavour or fragrance.

17. The method of claim 6, wherein the first co-monomer is an isocyanate; the benefit agent is an organoleptic benefit agent; and the radical initiator is at least one of peroxide or azo-.

18. The method of claim 6, wherein the second co-monomer is:
    at least one of diol or diamine and
    capable of forming a polyurethane or polyuria on reaction with the first comonomer.

19. The method of claim 7, wherein the at least one monomer is at least one of acrylate or methacryate.

* * * * *